(12) United States Patent
Lingnau et al.

(10) Patent No.: US 7,858,588 B2
(45) Date of Patent: Dec. 28, 2010

(54) IMMUNOSTIMULATORY OLIGODEOXYNUCLEIC MOLECULES

(75) Inventors: Karen Lingnau, Vienna (AT); Carola Schellack, Vienna (AT); Walter Schmidt, Vienna (AT)

(73) Assignee: Intercell AG, Vienna (AT)

( * ) Notice: Subject to any disclaimer, the term of this patent is extended or adjusted under 35 U.S.C. 154(b) by 799 days.

(21) Appl. No.: 10/478,771

(22) PCT Filed: May 17, 2002

(86) PCT No.: PCT/EP02/05448

§ 371 (c)(1), (2), (4) Date: Nov. 21, 2003

(87) PCT Pub. No.: WO02/095027

PCT Pub. Date: Nov. 28, 2002

(65) Prior Publication Data

US 2004/0248831 A1 Dec. 9, 2004

(30) Foreign Application Priority Data

May 21, 2001 (AT) ................................ A 805/2001

(51) Int. Cl.
*A01N 31/70* (2006.01)
*A61K 39/00* (2006.01)
*A61K 45/00* (2006.01)
*C12N 5/00* (2006.01)

(52) U.S. Cl. .................... 514/44; 424/184.1; 424/280.1; 435/375

(58) Field of Classification Search ........................ None
See application file for complete search history.

(56) References Cited

U.S. PATENT DOCUMENTS

| 3,725,545 | A | 4/1973 | Maes .......................... 424/180 |
| 3,906,092 | A * | 9/1975 | Hilleman et al. .......... 424/209.1 |
| 2002/0132995 | A1* | 9/2002 | Agrawal et al. ............. 536/23.1 |
| 2003/0171321 | A1 | 9/2003 | Schmidt et al. ................ 514/44 |

FOREIGN PATENT DOCUMENTS

| EP | 0 468 520 | 1/1992 |
| WO | WO 96/02555 | 2/1996 |
| WO | WO 98/16247 | 4/1998 |
| WO | WO 98/18810 | 5/1998 |
| WO | WO 98/37919 | 9/1998 |
| WO | WO 98/40100 | 9/1998 |
| WO | WO 98/52581 | 11/1998 |
| WO | WO 98/55609 | 12/1998 |
| WO | WO 99/51259 | 10/1999 |
| WO | WO 99/56755 | 11/1999 |
| WO | WO 01/93905 | 6/2001 |
| WO | WO 01/83503 | 11/2001 |
| WO | WO 02/069369 | 9/2002 |
| WO | WO 03/047602 | 6/2003 |

OTHER PUBLICATIONS

Trip et al. Nucleic Acids Research. vol. 5, No. 5, pp. 1539-1549. May 1978.*
Andreu and Rivas, "Animal antimicrobial peptides: an overview," *Biopoly*, 47:415-433, 1998.
Bailly et al., "PCR-based development of DNA substrates containing modified bases: an efficient system for investigating the role of the exocyclic groups on chemical and structural recognition by minor groove binding drugs and proteins," *Proc. Natl. Acad. Sci., USA*, 93:13623-13628, 1996.
Ballas et al., "Induction of NK activity in murine and human cells by CpG motif in oligodeoxynucleotides and bacterial DNA," *J. Immunol.*, 157:1840-1845, 1996.
Bloom et al., "Identification of tyrosinase-related protein 2 as a tumor rejection antigen for the B16 melanoma," *J. of Exp. Med.*, 185:453-459, 1997.
Buschle et al., "Chemically defined, cell-free cancer vaccines: use of tumor antigen-derived peptides or polyepitope proteins for vaccination," *Gene Ther. Mol. Biol.*, 1:309-321, 1998.
Buschle et al., "Transloading of tumor antigen-derived peptides into antigen-presenting cells," *Proc. Natl. Acad. Sci., USA*, 94:3256-3261, 1997.
Cavanaugh et al., "The activation of murine macrophages and natural killer cells by the partially thiolated double stranded RNA poly(I)-mercapto Poly (C)," *Research Communications in Molecular Pathology and Pharmacology*, 91:131-147, 1996.
Chace et al., "Bacterial DNA-induced NK cell IFN-gamma production is dependent on macrophage secretion of IL- 12," *Clin. Immunol. Immunopathol.*, 84:185-193, 1997.
Davis, "CpG DNA is a potent enhancer of specific immunity in mice immunized with recombinant hepatitis B surface antigen," *J. of Immunology*, 160:870-876, 1998.
Deng et al., "Intra-articularly localized bacterial DNA containing CpG motifs induces arthritis," *Nat. Medicine*, 5:702-705, 1999.

(Continued)

*Primary Examiner*—Janet L. Epps-Smith
(74) *Attorney, Agent, or Firm*—Fulbright & Jaworski LLP

(57) ABSTRACT

Described is an immunostimulatory oligodeoxynucleic acid molecule (ODN) having the structure according to formula (I), wherein any X is O or S, any NMP is a 2' deoxynucleoside monophosphate or monothiophosphate, selected from the group consisting of deoxyadenosine-, deoxyguanosine-, deoxyinosine-, deoxycytosine-, deoxyuridine-, deoxythymidine-, 2-methyl-deoxyinosine-, 5-methyl-deoxycytosine-, deoxypseudouridine-, deoxyribosepurine-, 2-amino-deoxyribosepurine-, -6-S-deoxyguanine-, 2-dimethyl-deoxyguanosine- or N-isopentenyl-deoxyadenosine-monophosphate or -monothiophosphate, NUC is a 2' deoxynucleoside, selected from the group consisting of deoxyadenosine-, deoxyguanosine-, deoxyinosine-, deoxycytosine-, deoxyuridine-, deoxythymidine-, 2-methyl-deoxyinosine-, 5-methyl-deoxycytosine-, deoxypseudouridine-, deoxyribosepurine-, 2-amino-deoxyribosepurine-, 6-S-deoxyguanine-, 2-dimethyl-deoxyguanosine- or N-isopentenyl-deoxyadenosine, any X is O or S, a and b integers from 0 to 100 with the proviso that a+b is between 4 and 150, B and E are common groups for 5' or 3' ends of nucleic acid molecules, as well as a pharmaceutical composition containing such ODNs.

26 Claims, 9 Drawing Sheets

OTHER PUBLICATIONS

Ganz and Lehrer, "Antibiotic peptides from higher eukaryotes: biology and applications," *Molecular Medicine Today*, 5:292-297, 1999.

Ganz, "Enhanced: defensins and host defense," *Science*, 286:420-421, 1999.

Hancock, "Host defence (cationic) peptides. What is their future clinical potential?" *Drugs*, 57:469-473, 1999.

Hartmann, "CpG DNA: a potent signal for growth, activation, and maturation of human dendritic cells," *Proc. Natl. Acad. Sci., USA*, 96:9305-9310, 1999.

Hoffmann et al., "Phylogenetic perspectives in innate immunity," *Science*, 284:1313-1317, 1999.

Hwang and Greenberg, "Synthesis of 2'-modified oligodeoxynucleotides via on-column conjugation," *J. Org. Chem.*, 66(2):363-369, 2001.

Kandimalla et al., "Effect of chemical modifications of cytosine and guanine in a CpG-motif of oligonucleotides: structure-immunostimulatory activity relationships," *Bioorganic & Medicinal Chemistry*, 9:807-813, 2001.

Klinman et al., "CpG motifs present in bacterial DNA rapidly induce lymphocytes to secrete interleukin 6, interleukin 12, and interferon γ," *Proc. Natl. Acad. Sci., USA*, 93:2879-2883, 1996.

Krieg et al., "CpG motifs in bacterial DNA trigger direct B-cell activation," *Nature*, 374:546-549, 1995.

Krieg et al., "The role of CpG dinucleotides in DNA vaccines," *Trends in Microbiology*, 6:23-27, 1998.

Krieg, "CpG DNA: a novel immunomodulator," *Trends in Microbiology*, 7:64, 1999.

Lethe, "Mouse tumor rejection antigens P815A and P815B: two epitopes carried by a single peptide," *Eur. J. Immunol.*, 22:2283-2288, 1992.

Liljeqvist and Stahl, "Production of recombinant subunit vaccines; protein immunogens, live delivery systems and nucleic acid vaccines," *J. of Biotechnology*, 73:1-33, 1999.

Lipford et al., "Bacterial DNA as immune cell activator," *Trends Microbiol.*, 6:496-500, 1998.

Manetti et al., "Polyinosinic acid: polycytidylic acid promotes T helper type 1-specific immune response by stimulating macrophage production of interferon-α and interleukin-12," *Eur J. Immunol.*, 25:2656-2660, 1995.

Nomura et al., "Site-specific introduction of functional groups into phosphodiester oligodeoxynucleotides and their thermal stability and nuclease-resistance properties," *Nucleic Acids Research*, 25(14):2784-2791, 1997.

Oxenius et al., "CpG-containing oligonucleotides are efficient adjuvants for induction of protective antiviral immune responses with T-cell peptide vaccines," *J of Virology*, 73:4120-4126, 1999.

Ozaki et al., "Effect of acridine with various linker arms attached to C5 position of 2'-deoxyuridine on the stability of NDA/DNA and DNA/RNA duplexes," *Nucleosides & Nucleotides*, 17(5): 911-923, 1998.

Ozaki et al., "Post-synthetic functionalization of oligodeoxyribonucleotides at the 2'-position," *Tetrahedron Letters*, 42:677-680, 2001.

Parronchi et al., "Phosphorothioate oligodeoxynucleotides promote the in vitro development of human allergen-specific CD4+ T cells into Th1 effectors," *J. Immunol.*, 163:5946-5953, 1999.

Pisetsky, "Immunostimulatory DNA: a clear and present danger?" *Nature Medicine*, 3:829831, 1997.

Pisetsky, "The influence of base sequence on the immunostimulatory properties of DNA," *Immunol. Res.*, 19:35-46, 1999.

Rodrigues et al., "The in vivo cytotoxic activity of CD8+ T cell clones correlates with their levels of expression of adhesion molecules," *J. Exp. Med.*, 175:895-905, 1992.

Schmidt et al., "Cell-free tumor antigen peptide-based cancer vaccines," *Proc. Natl. Acad. Sci., USA*, 94:3262-3267, 1997.

Seela and He, "2'-deoxyuridine and 2'-deoxyisocytidine as constituents of DNA with parallel chain oreintation: the stabilization of the iCd. Gd base pair by the 5-methyl group," *Helvetical Chimica Acta*, 83:2527-2540, 2000.

Shinozuka et al., "Multi-functionalization of oligodeoxynucleotide: a facile post-synthetic modification technique for the preparation of oligodeoxynucleotides with two different functional molecules," *Chemical Communications*, 1:59-60, 2000.

Simmaco et al., "Antimicrobial peptides form amphibian skin: what do they tell us?" *Biopolymers*, 47:435-450, 1998.

Sparbier and Walden, "T cell receptor specificity and mimotopes," *Current Opinion in Immunology*, 11:214-218, 1999.

Sparwasser et al., "Bacterial DNA and immunostimulatory CpG oligonucleotides trigger maturation and activation of murine dendritic cells," *Eur. J. Immunol.*, 28:2045-2054, 1998.

Sparwasser et al., "Bacterial DNA causes septic shock," *Nature*, 386:336-337, 1997.

Sparwasser et al, "Macrophages sense pathogens via DNA motifs: induction of tumor necrosis factor-α-mediated shock," *Eur. J. Immunol.*, 27:1671-1679, 1997.

Ueno et al., "Effects of 5-(N-aminohexyl)carbamoyl]-2'-deoxyuridine on endonuclease stability and the ability of oligodeoxynucleotide to activate Rnase H," *Nucleic Acids Research*, 25(19), 3777-3782, 1997.

Ueno et al., "Nucleosides and nucleotides. 170. Synthesis and properties of oligodeoxynucleotides containing 5-[N[2-[N,N-Bis(3-aminopropyl)-amino]propyl]carbamoyl]2'deoxyuridine," *Bioconjugate Chem.*, 9:33-39, 1998.

Weiner et al., "Immunostimulatory oligodeoxynucleotides containing the CpG motif are effective as immune adjuvants in tumor antigen immunization," *Proc. Natl. Acad. Sci., USA*, 94:10833-10837, 1997.

\* cited by examiner

IMMUNOSTIMULATORY OLIGODEOXYNUCLEIC MOLECULES

This application is a U.S. national phase application under 35 U.S.C. §371 of International Application No. PCT/EP02/05448 filed 17 May 2002, which claims priority to Austrian Application No. A 805/2001 filed 21 May 2001.

The present invention relates to immunostimulatory oligodeoxynucleic molecules (ODNs) and pharmaceutical compositions containing such ODNs.

Vaccines can save more lives (and resources) than any other medical intervention (Nossal, 1998). Owing to worldwide vaccination programs the incidence of many fatal diseases has been decreased drastically. Although this notion is valid for a whole panel of diseases, e.g. tuberculosis, diphtheria, pertussis, measles and tetanus, there are no effective vaccines for numerous infectious disease including most viral infections, such as AIDS. There are also no effective vaccines for other diseases, infectious or non-infectious claiming millions the lives of millions of patients per year including malaria or cancer. In addition, the rapid emergence of antibiotic-resistant bacteria and microorganisms calls for alternative treatments with vaccines being a logical choice. Finally, the great need for vaccines is also illustrated by the fact that infectious diseases, rather than cardiovascular disorders or cancer or injuries remain the largest cause of death and disability in the world (Bloom and Widdus, 1998).

From an immunological point of view one major problem in the field of vaccines today is that traditional vaccines (and/or the immune-modulating compounds contained within these preparations) are designed to induce high levels of antibodies (Harrow and Lane, 1988). However, antibodies on their own are not effective in preventing a large number of diseases including most illnesses caused by viruses, intracellular bacteria, certain parasites and cancer. Examples for such diseases are, but are not restricted to, the above-mentioned HIV virus or *Plasmodium* spec. in case of malaria. In numerous experimental systems it has been shown that the cellular arm of the immune system, including T cells, rather than the humoral arm, is important for these indications. Therefore, novel, innovative technologies are needed to overcome the limitations of conventional vaccines. The focus must be on technologies that reliably induce the cellular immune system, including antigen specific T cells, which recognize molecules expressed on pathogen-infected cells. Ideally, vaccines are designed that induce both T cells distinguishing diseased and/or infected cells from normal cells and, simultaneously, antibodies secreted by B cells recognising pathogens in extracellular compartments.

Several established vaccines consist of live attenuated organism where the risk of reversion to the virulent wild-type strain exists. In particular in immunocompromised hosts this can be a live threatening scenario. Alternatively, vaccines are administered as a combination of pathogen-derived antigens together with compounds that induce or enhance immune responses against these antigens (these compounds are commonly termed adjuvant), since these subunit vaccines on their own are generally not effective.

Whilst there is no doubt that the above vaccines are valuable medical treatments, there is the disadvantage that, due to their complexity, severe side effects can be evoked, e.g. to antigens that are contained in the vaccine that display cross-reactivity with molecules expressed by cells of vaccinated individuals. In addition, existing requirements from regulatory authorities, e.g. the World Health Organization (WHO), the Food and Drug Administration (FDA), and their European counterparts, for exact specification of vaccine composition and mechanisms of induction of immunity, are difficult to meet.

Antigen presenting cells belong to the innate immune system, which has evolved as a first line host defence that limits infection early after exposure to microorganisms (Hoffmann et al., 1999). Cells of the innate immune system recognize patterns or relatively non-specific structures expressed on their targets rather than more sophisticated, specific structures which are recognised by the adaptive immune system (Hoffmann et al., 1999). Examples of cells of the innate immune system are macrophages and dendritic cells but also granulocytes (e.g. neutrophiles), natural killer cells and others. By contrast, cells of the adaptive immune system recognize specific, antigenic structures, including peptides, in the case of T cells and peptides as well as threedimensional structures in the case of B cells. The adaptive immune system is much more specific and sophisticated than the innate immune system and improves upon repeat exposure to a given pathogen/antigen. Phylogenetically, the innate immune system is much older and can be found already in very primitive organisms. Nevertheless, the innate immune system is critical during the initial phase of antigenic exposure since, in addition to containing pathogens, cells of the innate immune system, i.e. APCs, prime cells of the adaptive immune system and thus trigger specific immune responses leading to clearance of the intruders. In sum, cells of the innate immune system and in particular APCs play a critical role during the induction phase of immune responses by a) containing infections by means of a primitive pattern recognition system and b) priming cells of the adaptive immune system leading to specific immune responses and memory resulting in clearance of intruding pathogens or of other targets (Roitt et al., 1998). These mechanisms may also be important to clear or contain tumor cells.

As mentioned above, cells of the innate immune system recognise patterns expressed on their respective targets. Examples are lipopolysaccharides (LPS) in the case of Gram-negative bacteria, mycobacterial glycolipids, lipoteichoic acids of Gram-positive bacteria, mannans of yeast and double stranded RNAs of viruses (Hoffmann et al., 1999). In addition they may recognise patterns such as altered glycosylations of proteins on tumor cells.

Recent findings describe DNAs of protozoan or lower eukaryotes as a further pattern recognised by the innate (but possibly also by the adaptive) immune system of mammals (and probably most if not all vertebrates) (Krieg, 1996; Lipford et al., 1998).

The immune system recognises lower organisms including bacteria probably due to structural and sequence usage differencies between pathogen and host DNA. In particular short stretches of DNA, derived from non-vertebrates or in form of short synthetic ODNs containing nonmethylated cytosine-guanine dinucleotides (CpG) in a certain base context, are targeted (Krieg et al., 1995). CpG motifs are found at the expected frequency in bacterial DNA but are much less frequent in vertebrate DNA (Lipford et al., 1998; Pisetsky, 1999). In addition, non-vertebrate (i.e. bacterial) CpG motifs are not methylated whereas vertebrate CpG sequences are. These differences between bacterial. DNA and vertebrate DNA allow vertebrates to recognise non-vertebrate DNA as a danger signal.

Natural CpG-containing DNA, ODNs, as well as thiophosphate-substituted (exchange of thiophosphate residues for phosphate) ODNs containing CpG motifs (CpG-ODN) are not only potent activators of immune cell proliferation and humoral immune responses (Krieg et al., 1995), but also stimulate strong cellular immune responses (reviewed in Lipford et al., 1998). DNA/ODNs containing non-methylated CpG motifs can directly activate monocytic cells (dendritic cells, macrophages) and B cells. Likely, natural killer (NK) cells are not directly activated but respond to monocyte-derived IL-12 (interleukin 12) with a marked increase in their IFN-γ production (Chace et al., 1997). In consequence, the induction of monocytes and NK cells by CpG DNA promotes the induction of Th1-type responses and the development of cytotoxic T cells.

Ribonucleic acid based on inosine and cytosine, like polyinosinic-polycytidylic acid (poly I:C), is known to promote Th1-specific immune responses. It is known to stimulate macrophages to produce cytokines such as IL-1α and IL-12 (Manetti et al., 1995), it is also known as a potent interferon type 1 inducer (Manetti et al., 1995) and a potent NK cell stimulator (Cavanaugh et al., 1996).

This effect, however, was strictly restricted to ribonucleic acid containing inosine and cytidine residues (WO98/16247). Uridinecontaining ribonucleic acids have not been discussed in this connection so far.

Investigations by the inventors of the present invention showed that ODNs containing non-methylated CpG motifs, although being efficient in stimulating immune system, have essential disadvantages, especially with respect to specificity (high background) and induction of side effects, such as high systemic TNF-α production. High systemic TNF-α release is known to cause toxic shock syndrome, which can cause death of afflicted patients.

It is therefore an object of the present invention to provide suitable novel ODNs which do not have such drastic side effects as ODNs based on CpG sequences. It is a further object to reduce the side effects of pharmaceutical compositions containing known ODNs and to provide safe and efficient well-tolerable pharmaceutical compositions with efficient, immunostimulatory properties which are suitable for vaccination of animals, especially of mammals, including humans.

This object is solved by immunostimulatory oligodeoxynucleic acid molecule (ODN) having the structure according to formula (I)

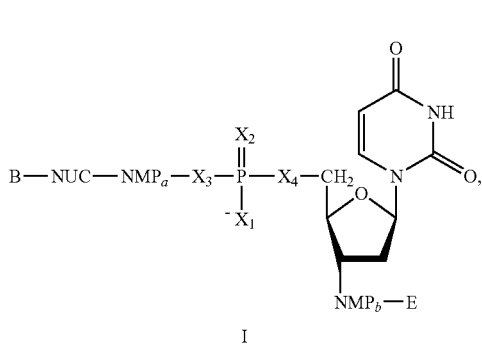

(I)

wherein any X is O or S, any NMP is a 2' deoxynucleoside monophosphate or monothiophosphate, selected from the group consisting of deoxyadenosine-, deoxyguanosine-, deoxyinosine-, deoxycytosine-, deoxyuridine-, deoxythymidine-, 2-methyl-deoxyinosine-, 5-methyl-deoxycytosine-, deoxypseudouridine-, deoxyribosepurine-, 2-amino-deoxyribosepurine-, 6-S-deoxyguanine-, 2-dimethyl-deoxygua-nosine- or N-isopentenyl-deoxyadenosine-monophosphate or -monothiophosphat, NUC is a 2' deoxynucleoside, selected from the group consisting of deoxyadenosine-, deoxyguanosine-, deoxyinosine-, deoxycytosine-, deoxyuridine-, deoxythymidine-, 2-methyl-deoxyinosine-, 5-methyl-deoxycytosine-, deoxypseudouridine-,deoxyribosepurine-, 2-amino-deoxyribosepurine-, 6-S-deoxyguanine-, 2-dimethyl-deoxyguanosine- or N-isopentenyl-deoxyadenosine, a and b are integers from 0 to 100 with the proviso that a+b is between 4 and 150, B and E are common groups for 5' or 3' ends of nucleic acid molecules.

Surprisingly it turned out that ODNs containing deoxyuridine residues (U-ODNs) show an immunostimulatory effect comparable or in many instances even better than ODNs containing CpG motifs. Compared to CpG-ODNs, ODNs according to the present invention induce comparable or higher numbers of specific T cells to a given antigen or antigen fragment. In addition, ODNs according to the present invention do not induce the systemic production of pro-inflammatory cytokines, such as TNF-α and IL-6, thus reducing the induction of potential harmful side reactions.

Whereas certain immunostimulatory effects had been described for inosine containing RNA molecules, such as poly-IC or the molecules mentioned in WO98/16247, it surprisingly turned out that deoxynucleic acid molecules containing deoxyuridine residues, may be good immunostimulating ODNs.

In addition, the U-ODNs according to the present invention are—in contrast to ODNs based on the specific CpG motif—not dependent on a specific motif or a palindromic sequence as described for the CpG oligonucleotides (see e.g. EP 0 468 520 A2, WO96/02555, WO98/18810, WO98/37919, WO98/40100, WO98/52581, WO99/51259 and WO99/56755, all incorporated herein by reference). Therefore, one group of U-ODNs according to the present invention may preferably contain a CU motif (and therefore ODNs described in these incorporated references, wherein one or more guanosine residues are replaced with deoxyuridine residues, are preferred embodiments of the present ODNs). It is not necessary for its principle immunostimulatory property, since U-ODNs with an Uridine not placed in a CU or UC context exhibit immunostimulatory properties as well.

The U-ODN according to the present invention is therefore a DNA molecule containing a deoxyuridine residue which is preferably provided in single stranded form.

The U-ODN according to the present invention may be isolated through recombinant methods or chemically synthesized. In the latter case, the U-ODN according to the present invention may also contain modified oligonucleotides which may be synthesized using standard chemical transformations, such as methylphosphonates or other phosphorous based modified oligonucleotides, such as phosphotriesters, phosphoamidates and phosphorodithiorates. Other non-phosphorous based modified oligonucleotides can also be used (Stirchak et al., MAR 17 (1989), 6129-6141), however, monophosphates or monothiophosphates being the preferred 2' deoxynucleoside monophosphate to be used in the present invention.

The NMPs of the U-ODNs according to the present invention are preferably selected from the group consisting of deoxyadenosine-, deoxyguanosine-, deoxyinosine-, deoxycytosine-, deoxyinosine-, deoxythymidine-, 2-methyl-deoxyuridine-, 5-methyl-deoxycytosinemonophosphate or -monothiophosphate (as usual, the phosphate or thiophosphate group is 5' of the deoxyribose). Whereas it is essential for the ODNs based on the CpG motif that this motif is unmethylated, this is surprisingly not the case for the ODNs according to the present invention, wherein e.g. 2-methyl-deoxyinosine or 5-methyl-deoxycytosine residues have no general negative effect on immunostimulatory properties of the ODNs according to the present invention. Alternatively, instead of the 2-deoxyforms of the NMPs, also other, especially inert, groups may be present at the 2-site of the ribose group, such as e.g. —F, —$NH_2$, —$CH_3$, especially —$CH_3$. Of course, —OH and SH groups are excluded for the U-ODNs according to the present invention to be present on the 2'-site of the ribose, especially the ribose residue for the uridine NMP.

The length of the ODNs according to the present invention is in the range of the standard ODNs used according to the prior art. Therefore molecules with a total length under 4 and above 150 show gradually decreasing immunostimulatory potential. Preferred ODNs contain between 10 and 60, especially between 15 and 40 bases (nucleosides), implying that a+b in formula I is between 10 and 60, preferably between 15 and 40 in these preferred embodiments.

Whereas the ribonucleic acid molecules containing inosine and cytidine described to be immunostimulatory in the prior art have been large and relatively undefined polynucleic acids with molecular weights far above 200,000 (a commercially available polyinosinic-polycytidylic acid from Sigma Chemicals has a molecular weight ranging from 220,000 to 460,000 (at least 500-1000 C+I residues). The molecules according to the present invention are DNA molecules of much shorter length with a well defined length and composition, being highly reproducible in products.

It is further preferred that the deoxyuridine containing NMP of the U-ODNs according to formula I is a monothiophosphate with one to four sulfur atoms and that also further NMPs, especially all further NMPs, are present as nucleoside monothiophosphates, because such ODNs display higher nuclease resistance (it is clear for the present invention that the "mono" in the "monothiophosphates" relates to the phosphate, i.e. that one phosphate group (one phosphor atom) is present in each NMP). Preferably, at least one of $X_1$ and $X_2$ is S and at least one of $X_3$ and $X_4$ is O in the NMPs according to the present invention. Preferably, $X_3$ and $X_4$ are O. ($X_3$ may be (due to synthesis of the NMP) derived e.g. from the phosphate group or from the 3'-group of the NMP-ribose).

Preferably the ODNs according to the present invention contain the sequence

```
tcc atg acu ttc ctg ctg atg ct    (SEQ ID NO: 1)

nhh hhh wdu dhh hhh hhh wn        (SEQ ID NO: 2)

hhh wdu dhh h                     (SEQ ID NO: 3)
``` wherein any n is a 2'-deoxynucleoside monophosphate or monothiophosphate, selected from the group consisting of deoxyadenosine-, deoxyguanosine-, deoxycytosine- or deoxythymidine-monophosphate or -monothiophosphate, any h is a T-deoxynucleoside monophosphate or monothiophosphate, selected from the group consisting of deoxyadenosine-, deoxycytosine- or deoxythymidine-monophosphate or monothiophosphate u is deoxyuridine-monophosphate or -monothiophosphate, any w is a 2'-deoxynucleoside monophosphate or monothiophosphate, selected from the group consisting of deoxyadenosine- or deoxythymidine-monophosphate or -monothiophosphate, and any d is a 2'-deoxynucleoside monophosphate or monothiophosphate, selected from the group consisting of deoxyadenosine-, deoxyguanosine- or deoxythymidine-monophosphate or monothiophosphate.

Further preferred ODNs according to the present invention contain the sequence
  wdu, wdud, wdudn or
  wdudud, wherein w, d, u and n are defined as above.

As outlined above, a specific motif (such as CpG or a palindrome) is not necessary for the U-ODNs according to the present invention.

However, ODNs containing a CU motif are preferred so that in a preferred embodiment the ODN according to formula I contains at least one 2' deoxycytosine-monophosphate or -monothiophosphate 3'-adjacent to a 2'-deoxyuridine-monophosphate or -monothiophosphate to form such a 5'-CU 3'-motif.

Preferred ODNs according to the present invention contain one or more of the sequence
  gacutt,
  uacutt,
  gauctt,
  uauctt, wherein a is deoxyadenosine-monophosphate or -monothiophosphate, g is deoxyguanosine-monophosphate or -monothiophosphate, u is deoxyuridine-monophosphate or -monothiophosphate, c is deoxycytosine-monophosphate or -monothiophosphate and t is deoxythymidine-monophosphate or -monothiophosphate.

The U-ODNs according to the present invention are especially suitable for application in the pharmaceutical field, e.g. to be applied as a medicine to an animal or to humans. They are specifically adapted to act as an immunostimulatory agent, especially in or together with vaccine compositions.

Therefore, the present invention also relates to a pharmaceutical composition comprising an ODN according to the present invention.

Since a preferred pharmaceutical composition according to the present invention is a vaccine, this composition should contain an antigen besides the ODN according to the present invention. The potential of this antigen to raise a protection/immune response of the vaccinated individual is strongly increased by combining it with the ODNs according to the present invention, especially due to their immunostimulatory activity.

A vaccine can contain a whole variety of different antigens. Examples of antigens are whole-killed organisms such as inactivated viruses or bacteria, fungi, protozoa or even cancer cells. Antigens may also consist of subfractions of these organisms/tissues, of proteins, or, in their most simple form, of peptides. Antigens can also be recognised by the immune system in form of glycosylated proteins or peptides and may also be or contain polysaccharides or lipids. Short peptides can be used since for example cytotoxic T cells (CTL) recognize antigens in form of short usually 8-11 amino acids long peptides in conjunction with major histocompatibility complex (MHC) (Rammensee et al., Immunogenetics 41, (1995), 178-228). B cells recognize longer peptides starting at around 15 amino acids (Harrow et al, Cold Spring Harbor: Cold Spring Harbor Laboratory, (1988)). By contrast to T cell epitopes, the three dimensional structure of B cell antigens may also be important for recognition by antibodies. In order to obtain sustained, antigen-specific immune responses, adjuvants are helpful to trigger immune cascades that involve all cells of the immune system necessary. Primarily, adjuvants are acting, but are not restricted in their mode of action, on so-called antigen presenting cells (APCs). These cells usually first encounter the antigen(s) followed by presentation of processed or unmodified antigen to immune effector. Intermediate cell types may also be involved. Only effector cells with the appropriate specificity are activated in a productive immune response. The adjuvant may also locally retain antigens and co-injected other factors. In addition the adjuvant may act as a chemoattractant for other immune cells or may act locally and/or systemically as a stimulating agent for the immune system.

The antigens to be used in the present compositions are not critical. Preferably, proteins or peptides derived from a viral or a bacterial pathogen or from fungi or parasites are used as such antigens (including derivatized antigens or glycosylated or lipidated antigens or polysaccharides or lipids). Another preferred source of antigens are tumor antigens. Preferred pathogens are selected from human immunodeficiency virus (HIV), hepatitis A and B viruses, hepatitis C virus (HCV), rous sarcoma virus (RSV), Epstein Barr virus (EBV) Influenza virus, Rotavirus, *Staphylococcus aureus, Chlamydia pneumonias, Chlamydia trachomatis, Mycobacterium tuberculosis, Streptococcus pneumonias, Bacillus anthracis, Vibrio cholerae, Plasmodium* sp. (*Pl. falciparum, Pl. vivax,* etc.), *Aspergillus* sp. or *Candida albicans*. Antigens may also be molecules expressed by cancer cells (tumor antigens). The derivation process may include the purification of a specific protein from the pathogen/cancer cells, the inactivation of the pathogen as well as the proteolytic or chemical derivatization or stabilisation of such a protein. In the same way also tumor antigens (cancer vaccines) or autoimmune antigens may be used in the pharmaceutical composition according to the present invention. With such compositions a tumor vaccination or a treatment for autoimmune diseases may be performed.

In the case of peptide antigens the use of peptide mimitopes/agonists/superagonists/antagonists or peptides changed in certain positions without affecting the immunologic properties or non-peptide mimitopes/agonists/superagonists/antagonists (reviewed in Sparbier and Walden, 1999) is included in the current invention. Peptide antigens may also contain elongations either at the carboxy or at the amino terminus of the peptide antigen facilitating interaction with the polycationic compound(s) or the immunostimulatory compound(s). For the treatment of autoimmune diseases peptide antagonists may be applied.

Antigens may also be derivatized to include molecules enhancing antigen presentation and targeting of antigens to antigen presenting cells.

In one embodiment of the invention the pharmaceutical composition serves to confer tolerance to proteins or protein fragments and peptides which are involved in autoimmune diseases. Antigens used in this embodiments serve to tolerize the immune system or down-regulate immune responses against epitopes involved in autoimmune processes.

Preferably the pharmaceutical composition according to the present invention, especially in the form of a vaccine, further comprises a polycationic polymer, preferably a polycationic peptide, especially polyarginine, polylysine or an antimicrobial peptide.

The polycationic compound(s) to be used according to the present invention may be any polycationic compound which shows the characteristic effect according to the WO 97/30721. Preferred polycationic compounds are selected from basic polypeptides, organic polycations, basic polyaminoacids or mixtures thereof. These polyaminoacids should have a chain length of at least 4 amino acid residues (see: Tuftsin as described in Goldman et al (1983)). Especially preferred are substances containing peptidic bounds, like polylysine, polyarginine and polypeptides containing more than 20%, especially more than 50% of basic amino acids in a range of more than 8, especially more than 20, amino acid residues or mixtures thereof. Other preferred polycations and their pharmaceutical compositons are described in WO 97/30721 (e.g. polyethyleneimine) and WO 99/38528. Preferably these polypeptides contain between 20 and 500 amino acid residues, especially between 30 and 200 residues.

These polycationic compounds may be produced chemically or recombinantly or may be derived from natural sources.

Cationic (poly)peptides may also be polycationic anti-bacterial microbial peptides with properties as reviewed in (Ganz and Lehrer, 1999; Hancock, 1999). These (poly)peptides may be of prokaryotic or animal or plant origin or may be produced chemically or recombinantly (Andreu and Rivas, 1998; Ganz and Lehrer, 1999; Simmaco et al., 1998). Peptides may also belong to the class of defensins (Ganz, 1999; Ganz and Lehrer, 1999). Sequences of such peptides can be, for example, be found in the Antimicrobial Sequences Database on the world wide web at bbcm.univ.trieste.it/~tossi/pag2.html.

Such host defense peptides or defensives are also a preferred form of the polycationic polymer according to the present invention. Generally, a compound allowing as an end product activation (or down-regulation) of the adaptive immune system, preferably mediated by APCs (including dendritic cells) is used as polycationic polymer.

Especially preferred for use as polycationic substance in the present invention are cathelicidin derived antimicrobial peptides or derivatives thereof (A 1416/2000, incorporated herein by reference), especially antimicrobial peptides derived from mammal cathelicidin, preferably from human, bovine or mouse, or neuroactive compounds, such as (human) growth hormone.

Polycationic compounds derived from natural sources include HIV-REV or HIVTAT (derived cationic peptides, antennapedia peptides, chitosan or other derivatives of chitin) or other peptides derived from these peptides or proteins by biochemical or recombinant production. Other preferred polycationic compounds are cathelin or related or derived substances from cathelin. For example, mouse cathelin is a peptide which has the amino acid sequence $NH_2$-RLAGLL-RKGGEKIGEKLKKIGQKIKNFFQKLVPQPE-COOH (SEQ ID NO:4. Related or derived cathelin substances contain the whole or parts of the cathelin sequence with at least 15-20 amino acid residues. Derivations may include the substitution or modification of the natural amino acids by amino acids which are not among the 20 standard amino acids. Moreover, further cationic residues may be introduced into such cathelin molecules. These cathelin molecules are preferred to be combined with the antigen and the immunogenic ODN according to the present invention. However, these cathelin molecules surprisingly have turned out to be also effective as an adjuvant for a antigen without the addition of further adjuvants. It is therefore possible to use such cathelin molecules as efficient adjuvants in vaccine formulations with or without further immunactivating substances.

Another preferred polycationic substance to be used according to the present invention is a synthetic peptide containing at least 2 KLK-motifs separated by a linker of 3 to 7 hydrophobic amino acids (A 1789/2000, incorporated herein by reference).

It was very surprising that the immunostimulating effect of the pharmaceutical composition according to the present invention was significantly higher than it could be expected from the addition of the effects of each single component or even the addition of the effects of the ODN or the polycation with the antigen.

B and E in formula I are common groups for 5' and/or 3' ends of nucleic acid molecules. Examples for such groups are readily available for the skilled man in the art (see e.g. "Oligonucleotides and Analogues—A Practical Approach" (1991), ed. Eckstein, Oxford University Press). For the U-ODNs according to the present invention B and/or E are preferably selected independently from —H, —$CH_3$, —$COCH_3$, —OH, —CHO, a phosphate, thiophosphate, sulfate or a thiosulfate group, or a phosphoalkylgroup, especially with an alkyl length of $C_1$-$C_6$ and/or with a terminal amino group (the amino group may e.g. be used for further labelling of the U-ODNs according to the present invention, e.g. —$PO_{4-}(CH_2)_n$—$NH_2$ or —$PO_4$—$(CH_2)_n$—NH-Label). Especially preferred as B are nucleosides, especially the 2' deoxynucleotides mentioned above (i.e. without the phosphate or thiophosphate group). Alternatively these groups may also contain linker groups to other molecules, especially carrier molecules or labels. In such forms of ODNs wherein the ODNs are bound to solid surfaces or particles or labels, these surfaces, particles, labels, etc. are then also part of the B and/or E groups.

Of course, any ionised (salt) form or tautomeric forms of the molecules according to formula I are included in this formula I.

The pharmaceutical composition according to the present invention may further comprise further active ingredients (pharmaceutically active substances), especially substances which are usable in a vaccine connection. Preferred embodiments of such further active ingredients are cytokines, antiinflammatory substances, antimicrobial substances or combinations thereof.

Of course, the pharmaceutical composition according to the present invention may further contain auxiliary substances, especially a pharmaceutically acceptable carrier, buffer substances, stabilizers or combinations thereof.

The relative amounts of the ingredients in the present pharmaceutical composition are highly dependent on the necessities of the individual antigen and on the animal/human to which this composition should be applied to. Therefore, the pharmaceutical composition according to the present invention preferably contains one or more ODNs according to the present invention, preferably 1 pg to 10 g, preferably 1 ng to 1 g, more preferred 100 ng to 10 mg, especially 10 µg to 1 mg. The antigen as well as the polycationic polymer may be applied in similar dosages, a range of 1 to 10,000 µg antigen and 0.1 to 1,000 µg polycation per vaccination is preferred.

The present compositions may be applied to a patient, e.g. a vaccination candidate, in efficient amounts e.g. by weekly, biweekly or monthly intervals. Patients to be treated with the present compositions may also be vaccinated repeatedly or only once. A preferred use of the present invention is the active immunisation, especially of humans or animals without protection against the specific antigen.

The route of application for the present composition is not critical, e.g. subcutaneous, intramuscular, intradermal or trans-dermal injection is suitable as well as oral uptake.

It is also possible to apply the present composition separatedly e.g. by injecting the immunostimulating substance separatedly from the antigen/polycation composition. The present invention is therefore also directed to a kit comprising a composition containing the antigen and the polycationic polymer as one component and a composition containing the immunostimulating or chemotactic substance as a second component.

The components may be applied at the same site or time, however, an application at different sites or at a different time or for a different time period is also possible. It is also possible to vary the systemic or local applications of the composition or the components, respectively.

The effectiveness of a immunostimulatory oligonucleotide according to the present invention per se is defined by the local availability of a minimally effective dose over a certain time range and is limited by the half-life of the oligonucleotide which is in vivo practically almost exclusively defined by the enzymatic degradation by nucleases. In order to safeguard the availability of the necessary dose over the necessary time range, (continuous) high-dosage administration regimen may be applied (such as e.g. during antisense therapy with oligonucleotides). A second preferred strategy is a stabilisation of the oligonucleotides against nuclease degradation by a phosphorothioate internucleotide bindings or by addition of polycations. As described in the examples, by providing only one of the stabilisation possibilities (e.g. preferably only phosphorothioate internucleotide bindings or addition of polycationic substances such as polyarginin) a high effectiveness is already available. However, effectiveness is even higher, if oligonucleotides are stabilised by both e.g. phosphorothioate internucleotide bindings and addition of polycationic substances (also leading to a fixation at the side of vaccination).

Details of the present invention are described by the following examples and the figures, but the invention is of course not limited thereto.

FIG. 1 shows that thiophosphate substituted deoxy-Uridin monophosphate modified oligodeoxynucleotides (U-ODN 13) induces in the presence or absence of poly-L-arginine a strong immune response against the melanoma-derived peptide TRP-$2_{181\text{-}188}$, which is higher than the immune response induced by CpG-ODN 1668 or CpG-ODN1668/poly-L-arginine. Furthermore, FIG. 1 shows that when U-ODNs, which are not substituted with thiophosphates (U-ODN 13b), were used only after co-injection of poly-L-arginine a strong peptide-specific immune response is induced. Mice were injected into the hind footpads with TRP-$2_{181\text{-}188}$, TRP-$2_{181\text{-}188}$ with either poly-L-arginine (pR60) or the U-containing oligodeoxynucleotide U-ODN 13/13b or with the combination of both, pR60 and U-ODN 13/13b. Four days later draining lymph node cells were ex vivo stimulated with TRP-$2_{181\text{-}188}$, an irrelevant peptide OVA$_{257\text{-}264}$, U-ODN 13/13b or pR60. The number of IFN-γ-producing cells was determined 24 hours later using an ELISPOT assay. Results are expressed as the number of IFN-γ-producing cells/$1\times10^6$ lymph node cells with standard deviation of triplicates.

FIG. 2 shows that the deoxy-Uridin monophosphate modified oligodeoxynucleotide (U-ODN 13) does not induce the systemic production of TNF-α and IL-6. Mice were injected into the hind footpads with TRP-$2_{181\text{-}188}$, TRP-$2_{181\text{-}188}$ and poly-L-arginine or CpG 1668 or U-ODN 13, or TRP-$2_{181\text{-}188}$ and the combination of poly-L-arginine and U-ODN 13. One hour after injection blood was taken from the tail vein and serum was prepared. The amount of TNF-α and IL-6 in the sera was determined using ELISAs.

FIG. 3 shows that deoxy-Uridin monophosphate modified oligodeoxynucleotides (U-ODN 13) induces an immune response against the ovalbumin-derived peptide OVA$_{257-264}$ (SIINFEKL, SEQ ID NO:8). Mice were injected into the hind footpads with OVA$_{257-264}$ alone, OVA$_{257-264}$ and poly-L-arginine (pR60) or the U-containing oligodeoxynucleotides U-ODN 13, or with OVA$_{257-264}$ and the combination of both, pR60 and U-ODN 13. Four days later, draining lymph node cells were ex vivo stimulated with OVA$_{257-264}$, an irrelevant peptide mTRP2$_{181-188}$ (murine tyrosinase related protein-2, VYDFFVWL, SEQ ID NO:5), U-ODN 13 and pR 60. The number of IFN-γ producing cells was determined 24 hours later using an ELISPOT assay. Results are expressed as the number of IFN-γ-producing cells/1×10$^6$ lymph node cells with standard deviation of duplicates.

FIG. 4 shows that deoxy-Uridin monophosphate modified oligodeoxynucleotides (U-ODN 13) induces a strong immune response against the mouse mastocytoma-derived peptide P1A$_{35-43}$ (LPYLGWLVF, SEQ ID NO:9), which can be further enhanced by co-injection of poly-L-arginine. Mice were injected into the hind footpads with P1A$_{35-43}$ alone, P1A$_{35-43}$ and poly-L-arginine or U-ODN 13, or with P1A$_{35-43}$ and the combination of both, pR60 and U-ODN 13. Four days later, draining lymph node cells were ex vivo stimulated with P1A$_{3543}$, an irrelevant peptide CSP (SYVPSAEQI, SEQ ID NO:18), U-ODN 13 and pR 60. The number of IFN-γ producing cells was determined 24 hours later using an ELISPOT assay. Results are expressed as the number of IFN-γ-producing cells/1×10$^6$ lymph node cells with standard deviation of triplicates.

FIG. 5 shows that a cocktail of deoxy-Uridin monophosphate modified oligodeoxynucleotides (U-ODN 15) induces in the presence or absence of poly-L-arginine a strong immune response against the melanoma-derived peptide TRP-2$_{181-188}$. Mice were injected into the hind footpads with TRP-2$_{181-188}$, TRP-2$_{181-188}$ with either poly-L-arginine (pR60) or the U-containing oligodeoxynucleotide coktail U-ODN 15 or with the combination of both, pR60 and U-ODN 15. Four days later draining lymph node cells were ex vivo stimulated with TRP-2$_{181-188}$, an irrelevant peptide OVA$_{257-264}$, U-ODN 15 or pR60. The number of IFN-γ-producing cells was determined 24 hours later using an ELISPOT assay. Results are expressed as the number of IFN-γ-producing cells/1×10$^6$ lymph node cells with standard deviation of triplicates.

FIG. 6 shows that a cocktail of deoxy-Uridin monophosphate modified oligodeoxynucleotides (U-ODN 16) induces a strong immune response against the melanoma-derived peptide TRP-2$_{181-188}$, which is higher compared to the immune response after injection of TRP-2$_{181-188}$ alone or in combination with ODN 20, an oligonucleotide cocktail without deoxy-Uridin monophosphate. Mice were injected into the hind footpads with TRP-2$_{181-188}$, TRP-2$_{181-188}$ with either the U-containing oligodeoxynucleotide coktail U-ODN 16 or the oligonucleotide cocktail ODN 20. Four days later draining lymph node cells were ex vivo stimulated with TRP-2$_{181-188}$, an irrelevant peptide OVA$_{257-264}$, U-ODN 16 or ODN 20. The number of IFN-γ-producing cells was determined 24 hours later using an ELISPOT assay. Results are expressed as the number of IFN-γ-producing cells/1×10$^6$ lymph node cells with standard deviation of triplicates.

EXAMPLES

If not otherwise mentioned, in all experiments thiophosphate-substituted ODNs (with thiophosphate residues substituting for phosphate, hereafter called "thiophosphate substituted oligodeoxynucleotides") were used since such ODNs display higher nuclease resistance (Ballas et al., 1996; Krieg et al., 1995; Parronchi et al., 1999).

Example 1

Generation of Specific Immune Responses Against a Melanoma-Derived Peptide (TRP-2$_{181-188}$) with deoxy-Uridine Monophosphate Modified Oligonucleotide U-ODN 13

| | |
|---|---|
| Mice | C57Bl/6 (Harlan/Olac) |
| Peptide | TRP-2-peptide (VYDFFVWL, SEQ ID NO:5), a MHC class I (H-2Kb)-restricted epitope of mouse tyrosinase related protein-2 (B16 melanoma, Bloom, M. B. et al., J Exp. Med 1997, 185, 453-459), synthesized by standard solid phase F-moc synthesis, HPLC purified and analysed by mass spectroscopy for purity Dose: 100 μg/mouse |
| Poly-L-arginine 60 (pR60) | Poly-L-arginine with an average degree of polymerization of 60 Dose: 100 μg/mouse |
| CpG 1668 | thiophosphate substituted ODNs containing CpG-motif: tcc atg acg ttc ctg atg ct (SEQ ID NO:6), were synthesized by NAPS GmbH, Göttingen. Dose: 5 nmol/mouse |
| U-ODN 13 | thiophosphate substituted ODNs containing deoxy-Uridine monophosphate: tcc atg acu ttc ctg atg ct (SEQ ID NO:1), were synthesized by NAPS GmbH, Göttingen. Dose: 5 nmol/mouse |
| U-ODN 13b | ODNs containing deoxy-Uridine monophosphate (not substituted with thiophospate): tcc atg acu ttc ctg atg ct (SEQ ID NO:1), were synthesized by NAPS GmbH, Göttingen. Dose: 5 nmol/mouse |

Experimental Groups (4 Mice Per Group)

1. TRP-2$_{181-188}$
2. TRP-2$_{181-188}$+pR 60
3. TRP-2$_{181-188}$+CpG-ODN
4. TRP-2$_{181-188}$+U-ODN 13
5. TRP-2$_{181-188}$+U-ODN 13b
6. TRP-2$_{181-188}$+CpG-ODN+pR 60.
7. TRP-2$_{181-188}$+U-ODN 13+pR 60
8. TRP-2$_{181-188}$+U-ODN 13b+pR 60

Figure 1:
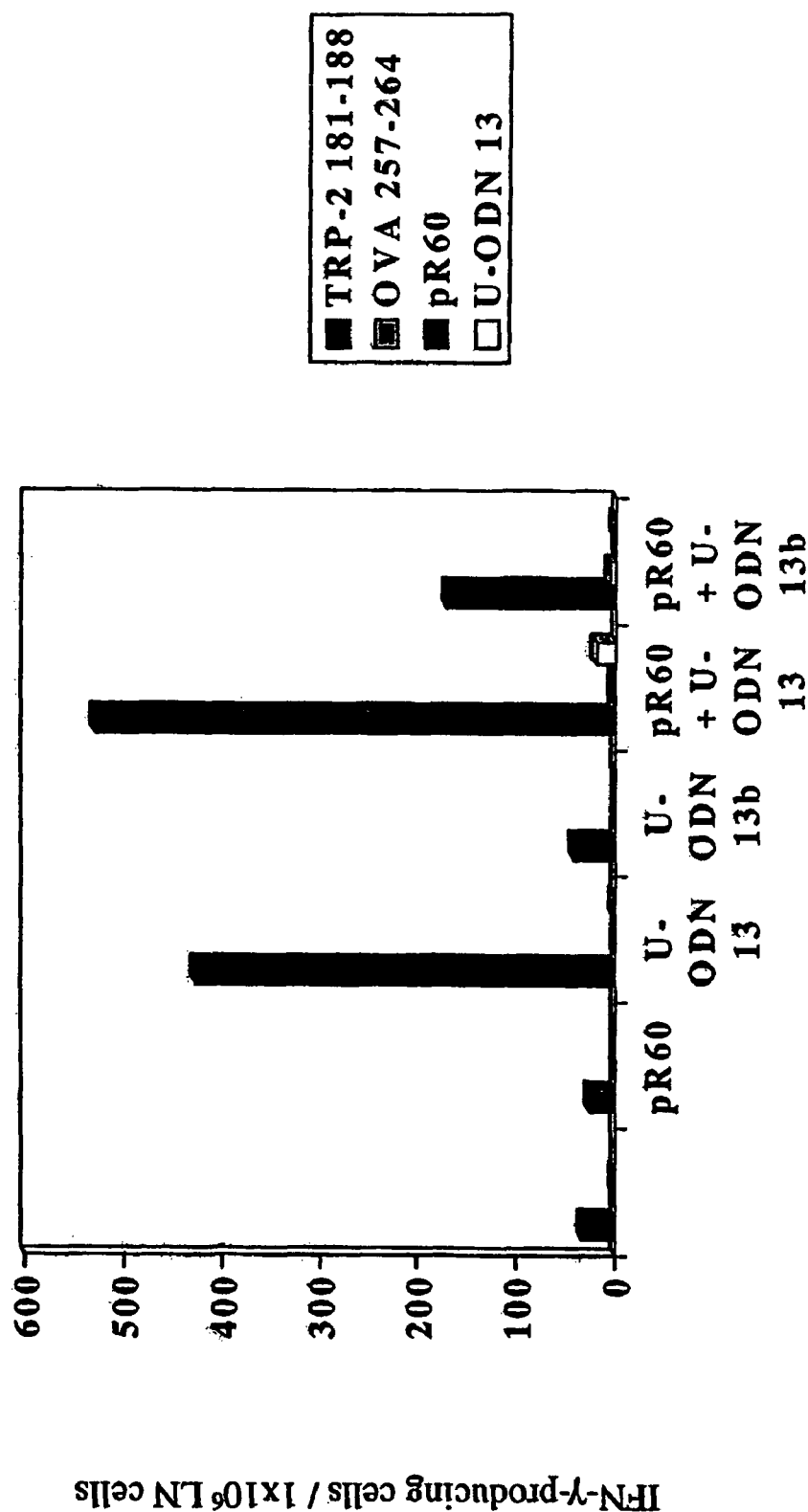

On day 0 mice were injected into each hind footpad with a total volume of 100 μl (50 μl per footpad) containing the above-mentioned compounds. Animals were sacrificed 4 days after injection and popliteal lymph nodes were harvested. Lymph nodes were passed through a 70 μm cell strainer and washed twice with DMEM medium (GIBCO BRL) containing 5% fetal calf serum (FCS, SIGMA chemicals). Cells were adjusted to the appropriate cell number in DMEM/5%/FCS. An IFN-γ ELISPOT assay was carried out in triplicates as described (Miyahira et al., 1995). This method is a widely used procedure allowing the quantification of antigen-specific T cells. Lymphocytes were stimulated ex vivo in triplicates with medium (background-control), TRP-2$_{181-188}$-peptide, an irrelevant peptide OVA$_{257-264}$, pR 60, U-ODN13 and Concanavalin A (Con A). Spots representing single IFN-γ producing T cells were counted and the number of background spots was substracted from all samples. The high number of spots detected after the stimulation with Con A (data not shown) indicates a good condition of the used lymphocytes. For each experimental group of mice the number of IFN-γ-producing cells/1×10$^6$ cells are illustrated in FIG. 1, the standard deviation of ex vivo-stimulated triplicates is given.

This experiment shows that the injection of TRP-2$_{181-188}$ (hydrophobic peptide) with thiophosphate substituted U-ODNs strongly enhances TRP-2$_{181-188}$-specific immune responses compared to the injection of TRP-2$_{181-188}$ alone. Interestingly, compared to the injection of TRP-2$_{181-188}$/CpG-ODN, higher number of TRP-2$_{181-8}$-specific T cells are induced by injection of TRP-2$_{181-188}$/U-ODN 13. The co-injection of poly-L-arginine does not influence this strong response. In contrast, when U-ODN 13b, which is not substituted with thiophosphates, was used, only upon co-injection of poly-L-arginine a high immune response was induced.

Example 2

Application of Deoxy-Uridine Monophosphate Modified Oligodeoxynucleotides Does not Induce the Production of Pro-Inflammatory Cytokines

| | |
|---|---|
| Mice | C57BI/6 (Harlan/Olac) |
| Peptide | TRP-2-peptide (VYDFFVWL, SEQ ID NO:5), a MHC class I (H-2Kb)-restricted epitope of mouse tyrosinase related protein-2 (B16 melanoma, Bloom, M. B. et al., J Exp. Med 1997, 185, 453-459), synthesized by standard solid phase F-moc synthesis, HPLC purified and analysed by mass spectroscopy for purity Dose: 100 μg/mouse |
| Poly-L-arginine 60 (pR60) | Poly-L-arginine with an average degree of polymerization of 60 Dose: 100 μg/mouse |
| CpG 1668 | thiophosphate substituted ODNs containing a CpG motif: tcc atg acg ttc ctg atg ct (SEQ ID NO:6), were synthesized by NAPS GmbH, Göttingen. Dose: 5 nmol/mouse |
| U-ODN 13 | thiophosphate substituted ODNs containing deoxy-Uridine monophosphate: tcc atg acu ttc ctg atg ct (SEQ ID NO:1), were synthesized by NAPS GmbH, Göttingen. Dose: 5 nmol/mouse |

Experimental Groups (4 Mice Per Group)

1. TRP-2$_{181-188}$

2. TRP-2$_{181-188}$+pR 60

3. TRP-2$_{181-188}$ CpG 1668

4. TRP-2$_{181-188}$+U-ODN 13

5. TRP-2$_{181-188}$+U-ODN 13+pR 60

On day 0 mice were injected into each hind footpad with a total volume of 100 μl (50 μl per footpad) containing the above-mentioned compounds. One hour after injection blood was taken via the tail vein and serum was prepared. The amount of TNF-α and IL-6 in the sera were determined by specific ELISAs.

Figure 2:
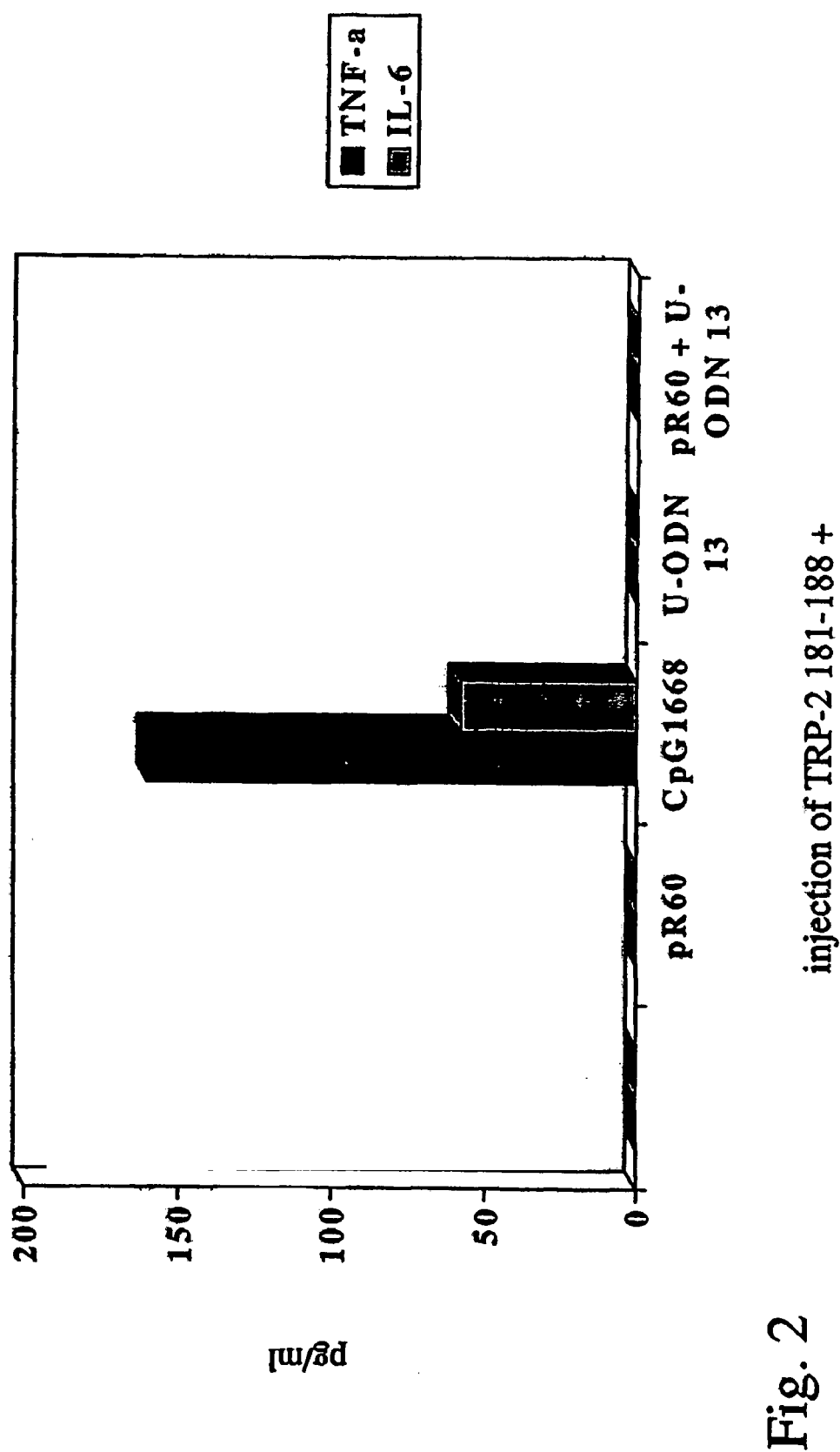

FIG. 2 shows that, in contrast to the application of CpG-ODN 1668 the application of U-ODN 13 in combination with a peptide does not induce the systemic production of pro-inflammatory cytokines.

Example 3

Generation of Specific Immune Responses Against an Allergen Derived Peptide with deoxy-Uridine Monophosphate Modified Oligonucleotide U-ODN 13

| | |
|---|---|
| Mice | C57BI/6 (Harlan/Olac) |
| Peptide | OVA$_{257-264}$-Peptide (SIINFEKL, SEQ ID NO:8), a MHC class I (H-2Kb)-restricted epitope of chicken ovalbumin (Rotzschke et al., 1991), was synthesized using standard solid phase F-moc chemistry synthesis, HPLC purified and analysed by mass spectroscopy for purity. Dose: 300 μg/mouse |
| Poly-L-arginine 60 (pR60) | Poly-L-arginine with an average degree of polymerization of 60 Dose: 100 μg/mouse |
| U-ODN 13 | thiophosphate substituted ODNs containing deoxy-Uridine monophosphate: tcc atg acu ttc ctg atg ct (SEQ ID NO:1), were synthesized by NAPS GmbH, Göttingen. Dose: 5 nmol/mouse |

Experimental Groups (4 Mice Per Group)

1. OVA$_{257-264}$

2. OVA$_{267-264}$+pR 60

3. OVA$_{267-264}$+U-ODN 13

4. OVA$_{257-264}$+U-ODN 13+pR 60

Figure 3:
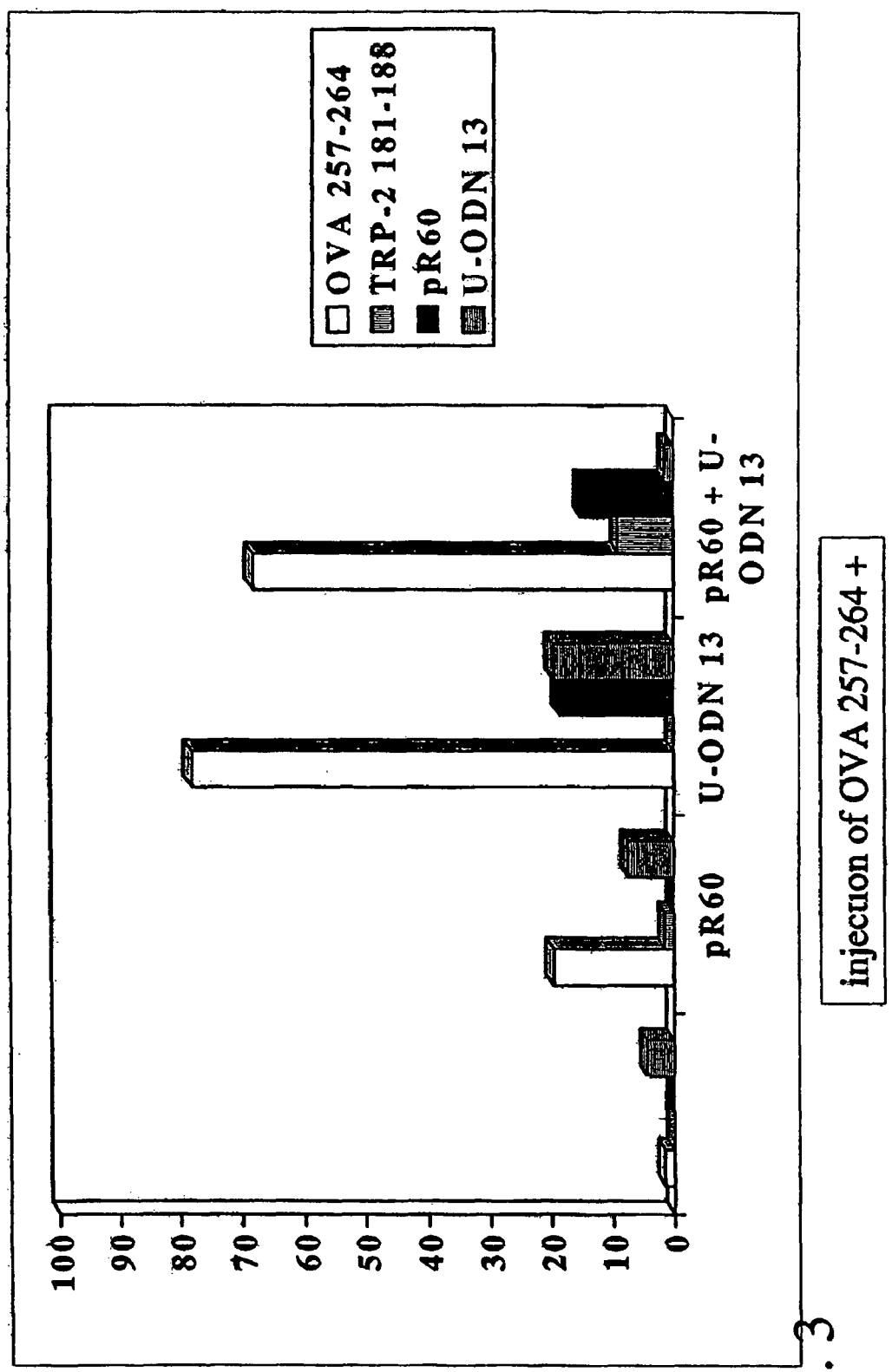

On day 0 mice were injected into each hind footpad with a total volume of 100 μl (50 μl per footpad) containing the above-mentioned compounds. Animals were sacrificed 4 days after injection and popliteal lymph nodes were harvested. Lymph nodes were passed through a 70 μm cell strainer and washed twice with DMEM medium (GIBCO BRL) containing 5% fetal calf serum (FCS, SIGMA chemicals). Cells were adjusted to the appropriate cell number in DMEM/5%/FCS. An IFN-γ ELISPOT assay was carried out in duplicates as described (Miyahira et al., 1995). This method is a widely used procedure allowing the quantification of antigen-specific T cells. Lymphocytes were stimulated ex vivo in duplicates with medium (background-control), OVA$_{257-264}$ peptide, an irrelevant peptide TRP-2$_{181-188}$, pR 60, U-ODN13 and Concanavalin A (Con A). Spots representing single IFN-γ producing T cells were counted and the number of background spots was substracted from all samples. The high number of spots detected after the stimulation with Con A (data not shown) indicates a good condition of the used lymphocytes. For each experimental group of mice the number of IFN-γ-producing cells/1×10$^6$ cells are illustrated in FIG. 3, the standard deviation of ex vivo-stimulated duplicates is given.

This experiment shows that deoxy-Uridine monophosphat modified ODNs also induces an immune response against a hydrophilic peptide (OVA$_{257-264}$). The co-injection of poly-L-arginine has no influence on this immune response.

Example 4

Generation of Specific Immune Responses Against a Mastocytoma-Derived Peptide with Deoxy-Uridine Monophosphate Modified Oligonucleotide U-ODN 13

| | |
|---|---|
| Mice | C57Bl/6 (Harlan/Olac) |
| Peptide | Mouse mastocytoma P815-derived peptide P1A (LPYLGWLVF, SEQ ID NO:9), restricted to MHC class I (H2-Ld) (Lethe et al., 1992). Dose: 100 µg/mouse |
| Poly-L-arginine 60 (pR60) | Poly-L-arginine with an average degree of polymerization of 60 Dose: 100 µg/mouse |
| U-ODN 13 | thiophosphate substituted ODNs containing deoxy-Uridine monophosphate: tcc atg acu ttc ctg atg ct (SEQ ID NO:1), were synthesized by NAPS GmbH, Göttingen. Dose: 5 nmol/mouse |

Experimental Groups (4 Mice Per Group)
1. P1A$_{35-43}$
2. P1A$_{35-43}$+pR 60
3. P1A$_{35-43}$+U-ODN 13
4. P1A$_{35-43}$+U-ODN 13+pR 60

Figure 4:
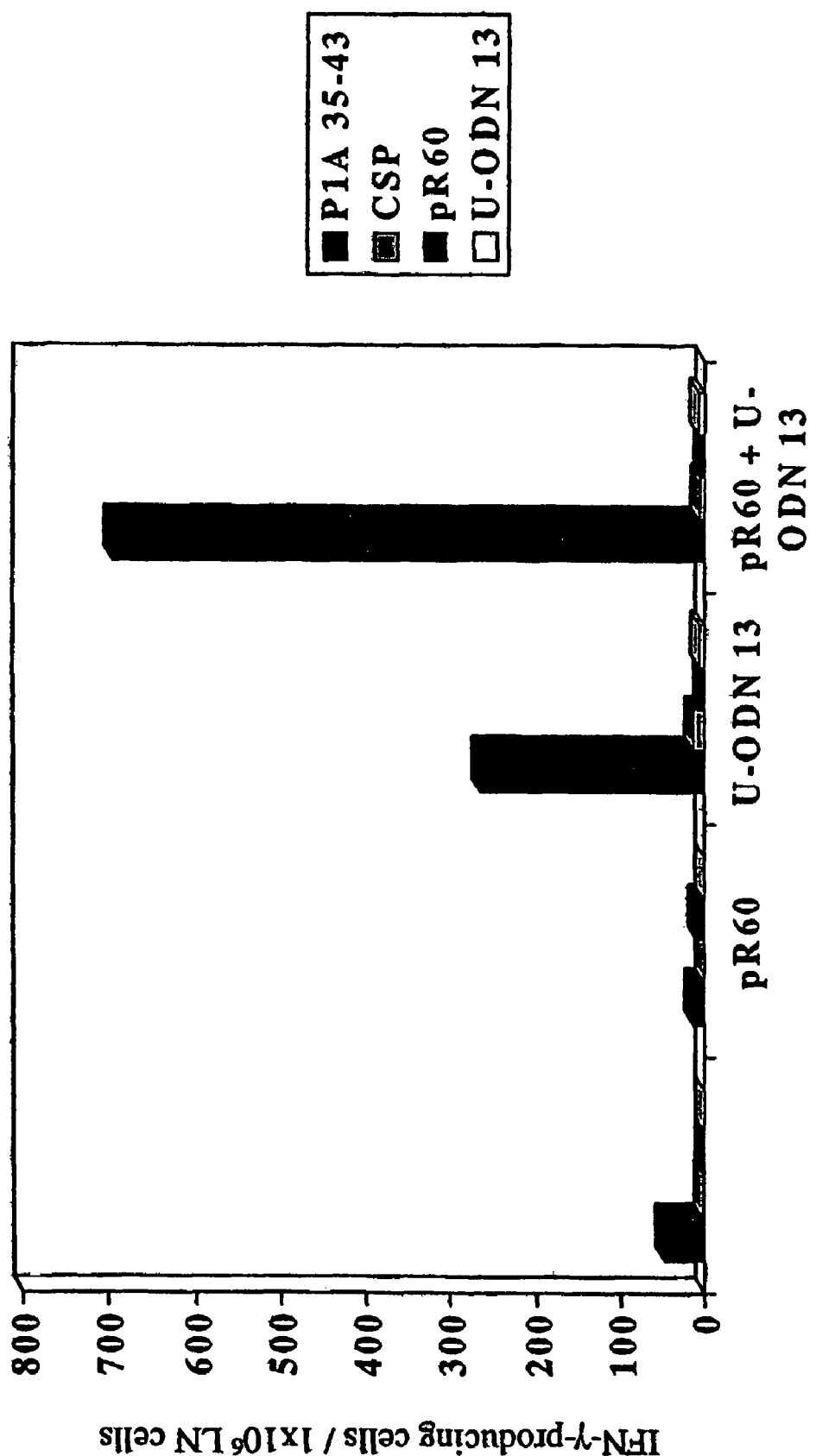

On day 0 mice were injected into each hind footpad with a total volume of 100 µl (50 µl per footpad) containing the above-mentioned compounds. Animals were sacrificed 4 days after injection and popliteal lymph nodes were harvested. Lymph nodes were passed through a 70 µm cell strainer and washed twice with DMEM medium (GIBCO BRL) containing 5% fetal calf serum (FCS, SIGMA chemicals). Cells were adjusted to the appropriate cell number in DMEM/5%/FCS. An IFN-γ ELISPOT assay was carried out in triplicates as described (Miyahira et al., 1995). This method is a widely used procedure allowing the quantification of antigen-specific T cells. Lymphocytes were stimulated ex vivo in triplicates with medium (background-control), P1A$_{35-43}$ peptide, an irrelevant peptide CSP (SYVPSAEQI, SEQ ID NO:18), pR 60, U-ODN 13 and Concanavalin A (Con A). Spots representing single IFN-γ producing T cells were counted and the number of background spots was substracted from all samples. The high number of spots detected after the stimulation with Con A (data not shown) indicates a good condition of the used lymphocytes. For each experimental group of mice the number of spots/1×10$^6$ cells are illustrated in FIG. 4, the standard deviation of ex vivo-stimulated triplicates is given.

This experiment shows that deoxy-Uridine monophosphate modified ODNs induces a strong immune response against the mastocytoma-derived peptide P1A$_{35-43}$. This response can be further enhanced by the co-application of poly-L-arginine.

Example 5

Induction of Specific Immune Responses Against a Melanoma-Derived Peptide (TRP-2$_{181-188}$) by a Cocktail of deoxy-Uridine Monophosphate Modified Oligonucleotides (U-ODN 15, 20mers)

In order to show that the effectiveness of an oligonucleotide on a deoxy-Uridine base according to the present invention is not dependent on the rest of the sequence (e.g. by a specific base, base motif or base sequence), a possibility would be to test each of these oligonucleotides in separated form, since this, however, is practically impossible (e.g. a 20mer would encompass 2,7×10$^{11}$ different sequences), in the present example another way was chosen to prove such an independence from the sequence. The aim of the present example was to test as many sequences as possible at once, since only the in vivo test and not the synthesis is limiting. For this reason, the present U-ODN 15 (see below) was made which contains more than nine billions different sequences. It follows that any single immunostimulatory sequence is diluted 10$^{-9}$ fold below any effective dose. Only the presence of deoxy-Uridine residues is constant in all sequences and therefore not diluted. If therefore sequence motifs beside deoxy-Uridine would be important for effectiveness in immunostimulatory oligonucleotides, they would be ineffective in U-ODN 15 due to the high dilution. On the other hand, if deoxy-Uridine is essential for the effectiveness and the rest of the sequence is not significant, U-ODN should be effective.

| | |
|---|---|
| Mice | C57Bl/6 (Harlan/Olac) |
| Peptide | TRP-2-peptide (VYDFFVWL, SEQ ID NO:5), a MHC class I (H-2Kb)-restricted epitope of mouse tyrosinase related protein-2 (B16 melanoma, Bloom, M. B. et al., J Exp. Med 1997, 185, 453-459), synthesized by standard solid phase F-moc synthesis, HPLC purified and analysed by mass spectroscopy for purity Dose: 100 µg/mouse |
| Poly-L-arginine 60 (pR60) | Poly-L-arginine with an average degree of polymerization of 60 Dose: 100 µg-0.1 µg/mouse |
| U-ODN 15 | Cocktail of thiophosphate substituted ODNs containing deoxy-Uridine monophosphate: nhh hhh wdu dhh hhh hhh wn (SEQ ID NO:2), were synthesized by NAPS GmbH, Göttingen. (n = GCAT, h = CAT, w = AT, d = GAT) Dose: 5 nmol-0.005 nmol/mouse |

Experimental Groups (4 Mice Per Group)
1. TRP-2$_{181-188}$
2. TRP-2$_{181-188}$+pR60 (100 µg)
3. TRP-2$_{181-188}$+U-ODN 15 (5 nmol)
4. TRP-2$_{181-188}$+U-ODN 15 (0, 5 nmol)
5. TRP-2$_{181-188}$+U-ODN 15 (0, 05 nmol)
6. TRP-2$_{181-188}$+U-ODN 15 (0, 005 nmol)
7. TRP-2$_{181-188}$+pR60 (100 µg)+U-ODN 15 (5 nmol)
8. TRP-2$_{181-188}$+pR60 (10 µg)+U-ODN 15 (0, 5 nmol)
9. TRP-2$_{181-188}$+pR60 (1 µg)+U-ODN 15 (0, 05 nmol)
10. TRP-2$_{181-188}$+pR60 (0, 1 µg)+U-ODN 15 (0, 005 nmol)

Figure 5:
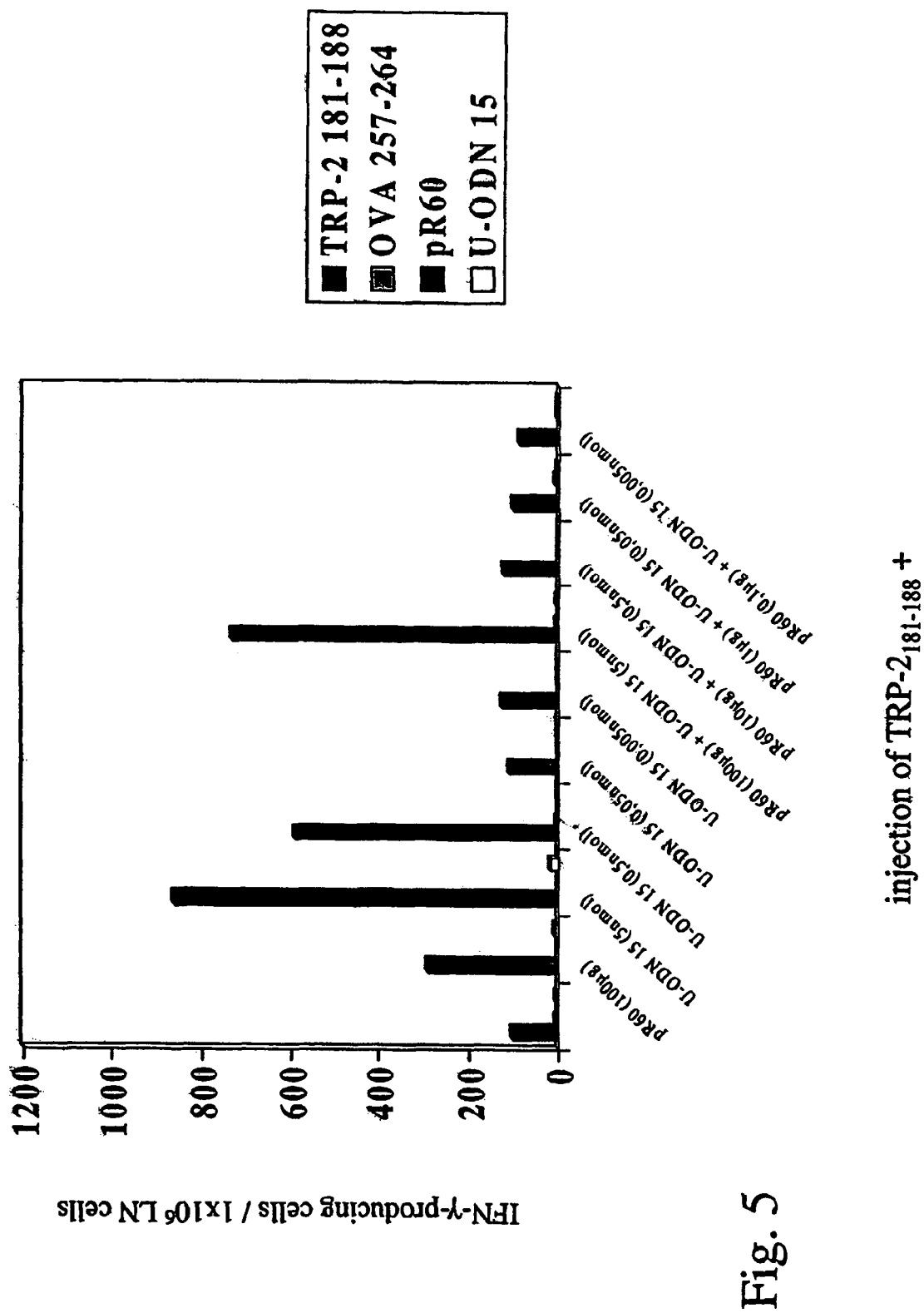

On day 0 mice were injected into each hind footpad with a total volume of 100 µl (50 µl per footpad) containing the above-mentioned compounds. Animals were sacrificed 4 days after injection and popliteal lymph nodes were harvested. Lymph nodes were passed through a 70 µm cell strainer and washed twice with DMEM medium (GIBCO BRL) containing 5% fetal calf serum (FCS, SIGMA chemicals). Cells were adjusted to the appropriate cell number in DMEM/5%/FCS. An IFN-γ ELISPOT assay was carried out in triplicates as described (Miyahira et al., 1995). This method is a widely used procedure allowing the quantification of antigen-specific T cells. Lymphocytes were stimulated ex vivo in triplicates with medium (background-control), TRP-2$_{181-188}$-peptide, an irrelevant peptide OVA$_{257-264}$, pR 60, U-ODN15 and Concanavalin A (Con A). Spots representing single IFN-γ producing T cells were counted and the number of background spots was substracted from all samples. The high number of spots detected after the stimulation with Con A (data not shown) indicates a good condition of the used lymphocytes. For each experimental group of mice the number of IFN-γ-producing cells/1×10⁶ cells are illustrated in FIG. 5, the standard deviation of ex vivo-stimulated triplicates is given.

This experiment shows that the injection of TRP-2$_{181-188}$ (hydrophobic peptide) with a cocktail of deoxy-Uridine monophosphate modified ODNs (20mers, 5 nmol) strongly enhances TRP-2$_{181-188}$-specific immune responses compared to the injection of TRP-2$_{181-188}$ alone. Even when 10 times less of the U-ODN 15 was used (0.5 nmol) a strong immune response could be induced. The co-injection of poly-L-arginine with peptide and U-ODN 15 (5 nmol) does not influence this strong response.

Example 6

Induction of Specific Immune Responses Against a Melanoma-Derived Peptide (TRP-2$_{181-188}$) by a Cocktail of deoxy-Uridine Monophosphate Modified Oligonucleotides (U-ODN 16, 10mers)

| | |
|---|---|
| Mice | C57Bl/6 (Harlan/Olac) |
| Peptide | TRP-2-peptide (VYDFFVWL, SEQ ID NO:5), a MHC class I (H-2Kb)-restricted epitope of mouse tyrosinase related protein-2 (B16 melanoma, Bloom, M. B. et al., J Exp. Med 1997, 185, 453-459), synthesized by standard solid phase F-moc synthesis, HPLC purified and analysed by mass spectroscopy for purity Dose: 100 µg/mouse |
| U-ODN 16 | Cocktail of thiophosphate substituted ODNs containing deoxy-Uridine monophosphate: hhh wdu dhh h (SEQ ID NO:3), were synthesized by NAPS GmbH, Göttingen. (n = GCAT, h = CAT, w = AT, d = GAT) Dose: 10 nmol/mouse |
| ODN 20 | Cocktail of thiophosphate substituted ODNs: hhh wdd dhh h (SEQ ID NO:19), were synthesized by NAPS GmbH, Göttingen. (n = GCAT, h = CAT, w = AT, d = GAT) Dose: 10 nmol/mouse |

Experimental Groups (4 Mice Per Group)

1. TRP-2$_{181-188}$
2. TRP-2$_{181-188}$+U-ODN 16 (10 nmol)
3. TRP-2$_{181-188}$ ODN 20 (10 nmol)

Figure 6:
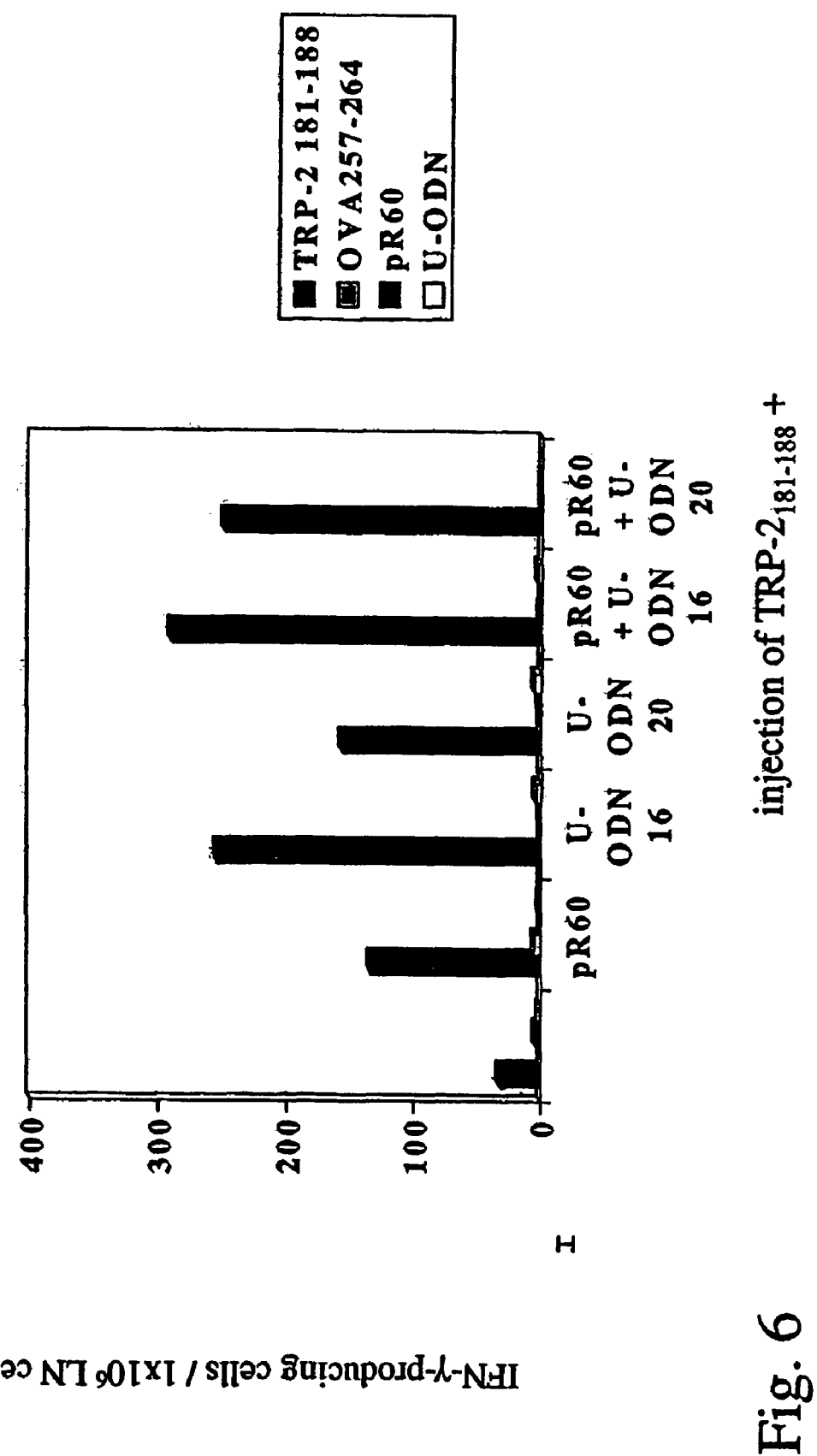

On day 0 mice were injected into each hind footpad with a total volume of 100 µl (50 µl per footpad) containing the above-mentioned compounds. Animals were sacrificed 4 days after injection and popliteal lymph nodes were harvested. Lymph nodes were passed through a 70 µm cell strainer and washed twice with DMEM medium (GIBCO BRL) containing 5% fetal calf serum (FCS, SIGMA chemicals). Cells were adjusted to the appropriate cell number in DMEM/5%/FCS. An IFN-γ ELISPOT assay was carried out in triplicates as described (Miyahira et al., 1995). This method is a widely used procedure allowing the quantification of antigen-specific T cells. Lymphocytes were stimulated ex vivo in triplicates with medium (background-control), TRP-2$_{181-188}$-peptide, an irrelevant peptide OVA$_{257-264}$, U-ODN 16, ODN 20 and Concanavalin A (Con A). Spots representing single IFN-γ producing T cells were counted and the number of background spots was substracted from all samples. The high number of spots detected after the stimulation with Con A (data not shown) indicates a good condition of the used lymphocytes. For each experimental group of mice the number of IFN-γ-producing cells/1×10⁶ cells are illustrated in FIG. 6, the standard deviation of ex vivo-stimulated triplicates is given.

This experiment shows that the injection of TRP-2$_{181-188}$ (hydrophobic peptide) with a cocktail of deoxy-Uridine monophosphate modified ODNs (10mers) strongly enhances TRP-2$_{181-188}$-specific immune responses compared to the injection of TRP-2$_{181-188}$ alone or in combination with ODN 20.

Example 7

Generation of Specific Immune Responses Against a Melanoma-Derived Peptide (TRP-2$_{181-188}$) with deoxy-Uridine Monophosphate Modified Oligonucleotide ODN 21 or ODN 22

| | |
|---|---|
| Mice | C57Bl/6 (Harlan/Olac) |
| Peptide | TRP-2-peptide (VYDFFVWL, SEQ ID NO:5), a MHC class I (H-2Kb)-restricted epitope of mouse tyrosinase related protein-2 (B16 melanoma, Bloom, M. B. et al., J Exp. Med 1997, 185, 453-459), synthesized by standard solid phase F-moc synthesis, HPLC purified and analysed by mass spectroscopy for purity Dose: 100 µg/mouse |
| Poly-L-arginine 60 (pR60) | Poly-L-arginine with an average degree of polymerization of 60 |
| ODN 21 | thiophosphate substituted ODNs containing deoxy-Uridine monophosphate: uau aua uau aua uau aua uau aua ua (SEQ ID NO:10), were synthesized by NAPS GmbH, Gottingen. Dose: 5 nmol/mouse |
| ODN 22 | thiophosphate substituted ODNs containing deoxy-Uridine monophosphate: uiu iui uiu iui uiu iui uiu iui ug (SEQ ID NO:20), were synthesized by NAPS GmbH, Gottingen. Dose: 5 nmol/mouse |

Experimental Groups (5 Mice Per Group)

1. TRP-2$_{181-188}$
2. TRP-2$_{181-188}$+pR 60
3. TRP-2$_{181-188}$+ODN 21
4. TRP-2$_{181-188}$+pR 60+ODN 21
5. TRP-2$_{181-188}$+ODN 22
6. TRP-2$_{181-188}$+pR 60+ODN 22

Figure 7:
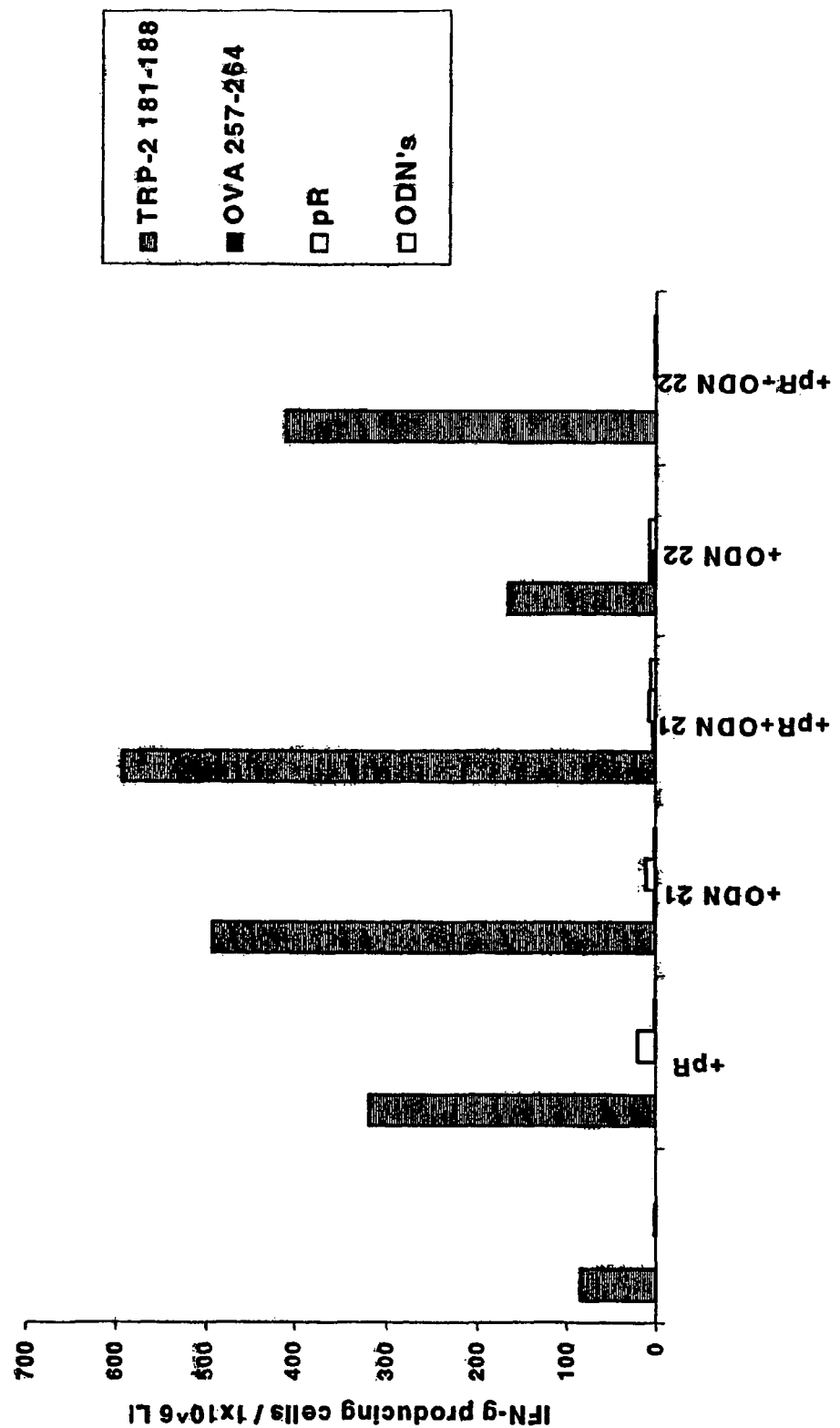
FIG. 7 shows the generation of specific immune responses against the melanoma-derived TRP-2$_{181-188}$ with U-ODN 21 and U-ODN 22.

On day 0 mice were injected into each hind footpad with a total volume of 100 µl (50 µl per footpad) containing the above-mentioned compounds. Animals were sacrificed 4 days after injection and popliteal lymph nodes were harvested. Lymph nodes were passed through a 70 µm cell strainer and washed twice with DMEM medium (GIBCO BRL) containing 5% fetal calf serum (FCS, SIGMA chemicals). Cells were adjusted to the appropriate cell number in DMEM/5%/FCS. An IFN-γ ELISPOT assay was carried out in triplicates as described (Miyahira et al., 1995). This method is a widely used procedure allowing the quantification of antigen-specific T cells. Lymphocytes were stimulated ex vivo in triplicates with medium (background-control), TRP-2$_{181-188}$-peptide, an irrelevant peptide OVA$_{257-264}$, pR 60, ODN 21 or 22 and Concanavalin A (Con A). Spots representing single IFN-γ producing T cells were counted and the number of background spots was substracted from all samples. The high number of spots detected after the stimulation with Con A (data not shown) indicates a good condition of the used lymphocytes. For each experimental group of mice the number of IFN-γ-producing cells/1×10⁶ cells are illustrated in FIG. 7, the standard deviation of ex vivo-stimulated triplicates is given.

Example 8

Generation of Specific Immune Responses Against a Melanoma-Derived Peptide (TRP-2₁₈₁₋₁₈₈) with deoxy-Uridine Monophosphate Modified Oligonucleotide ODN 24

| | |
|---|---|
| Mice | C57Bl/6 (Harlan/Olac) |
| Peptide | TRP-2-peptide (VYDFFVWL, SEQ ID NO:5), a MHC class I (H-2Kb)-restricted epitope of mouse tyrosinase related protein-2 (B16 melanoma, Bloom, M. B. et al., J Exp. Med 1997, 185, 453-459), synthesized by standard solid phase F-moc synthesis, HPLC purified and analysed by mass spectroscopy for purity Dose: 100 μg/mouse |
| Poly-L-arginine 60 (pR60) | Poly-L-arginine with an average degree of polymerization of 60 Dose: 100 μg/mouse |
| ODN 24 | thiophosphate substituted ODNs containing deoxy-Uridine monophosphate: uuu uuu uuu uuu uuu uuu uuu uuu ut (SEQ ID NO:12), were synthesized by NAPS GmbH, Gottingen. Dose: 5 nmol/mouse |

Experimental Groups (5 Mice Per Group)

1. TRP-2₁₈₁₋₁₈₈
2. TRP-2₁₈₁₋₁₈₈+pR 60
3. TRP-2₁₈₁₋₁₈₈+ODN 24
4. TRP-2₁₈₁₋₁₈₈+pR 60+ODN 24

Figure 8:
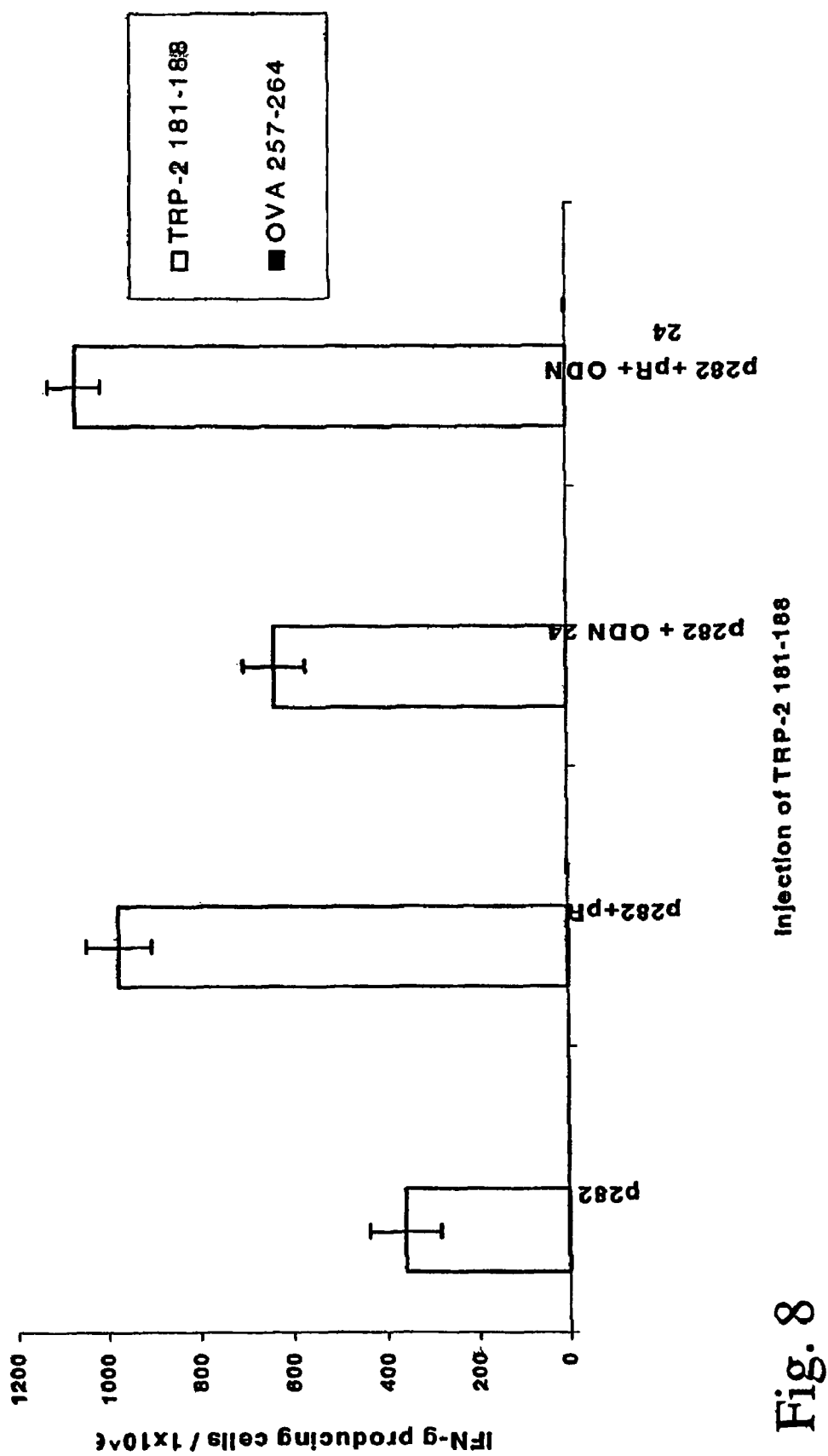
FIG. 8 shows the generation of specific immune responses against the melanoma-derived TRP-2$_{181-188}$ with U-ODN 24.

On day 0 mice were injected into each hind footpad with a total volume of 100 μl (50 μl per footpad) containing the above-mentioned compounds. Animals were sacrificed 4 days after injection and popliteal lymph nodes were harvested. Lymph nodes were passed through a 70 μm cell strainer and washed twice with DMEM medium (GIBCO BRL) containing 5% fetal calf serum (FCS, SIGMA chemicals). Cells were adjusted to the appropriate cell number in DMEM/5%/FCS. An IFN-γ ELISPOT assay was carried out in triplicates as described (Miyahira et al., 1995). This method is a widely used procedure allowing the quantification of antigen-specific T cells. Lymphocytes were stimulated ex vivo in triplicates with medium (background-control), TRP-2₁₈₁₋₁₈₈-peptide, an irrelevant peptide OVA₂₅₇₋₂₆₄, pR 60, ODN 24 and Concanavalin A (Con A). Spots representing single IFN-γ producing T cells were counted and the number of background spots was substracted from all samples. The high number of spots detected after the stimulation with Con A (data not shown) indicates a good condition of the used lymphocytes. For each experimental group of mice the number of IFN-γ-producing cells/1×10⁶ cells are illustrated in FIG. 8, the standard deviation of ex vivo-stimulated triplicates is given.

Example 9

Generation of Specific Immune Responses Against a Melanoma-Derived Peptide (TRP-2₁₈₁₋₁₈₈) with Different deoxy-Uridine Monophosphate Modified Oligonucleotides In order to further illustrate and strengthen the results of example 5, further examples on the basis of U-ODN 16 (as defined in example 6) have been carried out. For comparative reasons, variants have been used, wherein a specific base is not contained in the sequence. U-ODN 16-A does not contain adenine, U-ODN 16-C does not contain cytosine, U-ODNs 16-G contains no guanine, and U-ODN 16-T no thymine. If, beside deoxy-Uridine, a specific other base would be necessary for effectiveness, the corresponding oligonucleotide should not show any effectiveness. If, however, deoxy-Uridine is sufficient for efficacy, then IFN-γ producing Tcells are generated.

| | |
|---|---|
| Mice | C57Bl/6 (Harlan/Olac) |
| Peptide | TRP-2-peptide (VYDFFVWL, SEQ ID NO:5), a MHC class I (H-2Kb)-restricted epitope of mouse tyrosinase related protein-2 (B16 melanoma, Bloom, M. B. et al., J Exp. Med 1997, 185, 453-459), synthesized by standard solid phase F-moc synthesis, HPLC purified and analysed by mass spectroscopy for purity Dose: 100 μg/mouse |
| Poly-L-arginine 60 (pR60) | Poly-L-arginine with an average degree of polymerization of 60 Dose: 100 μg/mouse |
| ODN 16 | Cocktail of thiophosphate substituted ODNs containing deoxy-Uridine monophosphate: hhh wdu dhh h (SEQ ID NO:3), were synthesized by NAPS GmbH, Gottingen. (h = CAT, w = AT, d = GAT) Dose: 5 nmol/mouse |
| ODN 16-A | Cocktail of thiophosphate substituted ODNs containing deoxy-Uridine monophosphate: aaa bcu caa a (SEQ ID NO:13), were synthesized by NAPS GmbH, Gottingen. (a = CT, b = T, c = GT) Dose: 5 nmol/mouse |
| ODN 16-G | Cocktail of thiophosphate substituted ODNs containing deoxy-Uridine monophosphate: hhh wwu whh h (SEQ ID NO:14), were synthesized by NAPS GmbH, Gottingen. (h = CAT, w = AT) Dose: 5 nmol/mouse |
| ODN 16-C | Cocktail of thiophosphate substituted ODNs containing deoxy-Uridine monophosphate: www wdu dww w (SEQ ID NO:15), were synthesized by NAPS GmbH, Gottingen. (w = AT, d = GAT) Dose: 5 nmol/mouse |
| ODN 16-T | Cocktail of thiophosphate substituted ODNs containing deoxy-Uridine monophosphate: eee fgu gee e, were synthesized by NAPS GmbH, Gottingen. (e = CA, f = A, g = GA) Dose: 5 nmol/mouse |
| ODN 28 | Cocktail of thiophosphate substituted ODNs containing deoxy-Uridine monophosphate: hhh xdU dhh y (SEQ ID NO:17), were synthesized by NAPS GmbH, Gottingen. (h = CAT, x = T, d = GAT, y = GT) Dose: 5 nmol/mouse |

Experimental Groups (5 Mice Per Group)

1. TRP-2₁₈₁₋₁₈₈
2. TRP-2₁₈₁₋₁₈₈+pR 60
3. TRP-2₁₈₁₋₁₈₈+ODN 16
4. TRP-2₁₈₁₋₁₈₈+ODN 16-A
5. TRP-2₁₈₁₋₁₈₈+ODN 16-G
6. TRP-2₁₈₁₋₁₈₈+ODN 16-C
7. TRP-2₁₈₁₋₁₈₈+ODN 16-T
8. TRP-2₁₈₁₋₁₈₈+ODN 28
9. TRP-2₁₈₁₋₁₈₈+pR 60+ODN 16
10. TRP-2₁₈₁₋₁₈₈+pR 60+ODN 16-A

11. TRP-2$_{181-188}$+pR 60+ODN 16-G

12. TRP-2$_{181-188}$+pR 6.0+ODN 16-C

13. TRP-2$_{181-188}$+pR 60+ODN 16-T

14. TRP-2$_{181-188}$+pR 60+ODN 28

On day 0 mice were injected into each hind footpad with a total volume of 100 µl (50 µl per footpad) containing the above-mentioned compounds. Animals were sacrificed 4 days after injection and popliteal lymph nodes were harvested. Lymph nodes were passed through a 70 µm cell strainer and washed twice with DMEM medium (GIBCO BRL) containing 5% fetal calf serum (FCS, SIGMA chemicals). Cells were adjusted to the appropriate cell number in DMEM/5%/FCS. An IFN-γ ELISPOT assay was carried out in triplicates as described (Miyahira et al., 1995). This method is a widely used procedure allowing the quantification of antigen-specific T cells. Lymphocytes were stimulated ex vivo in triplicates with medium (background-control), TRP-2$_{181-188}$-peptide, an irrelevant peptide OVA$_{257-264}$, pR 60, the different ODNs and Concanavalin A (Con A). Spots representing single IFN-γ producing T cells were counted and the number of background spots was substracted from all samples. The high number of spots detected after the stimulation with Con A (data not shown) indicates a good condition of the used lymphocytes. For each experimental group of mice the number of IFN-γ-producing cells/1×10$^6$ cells are illustrated in FIG. 9, the standard deviation of ex vivo-stimulated triplicates is given.

Figure 9:
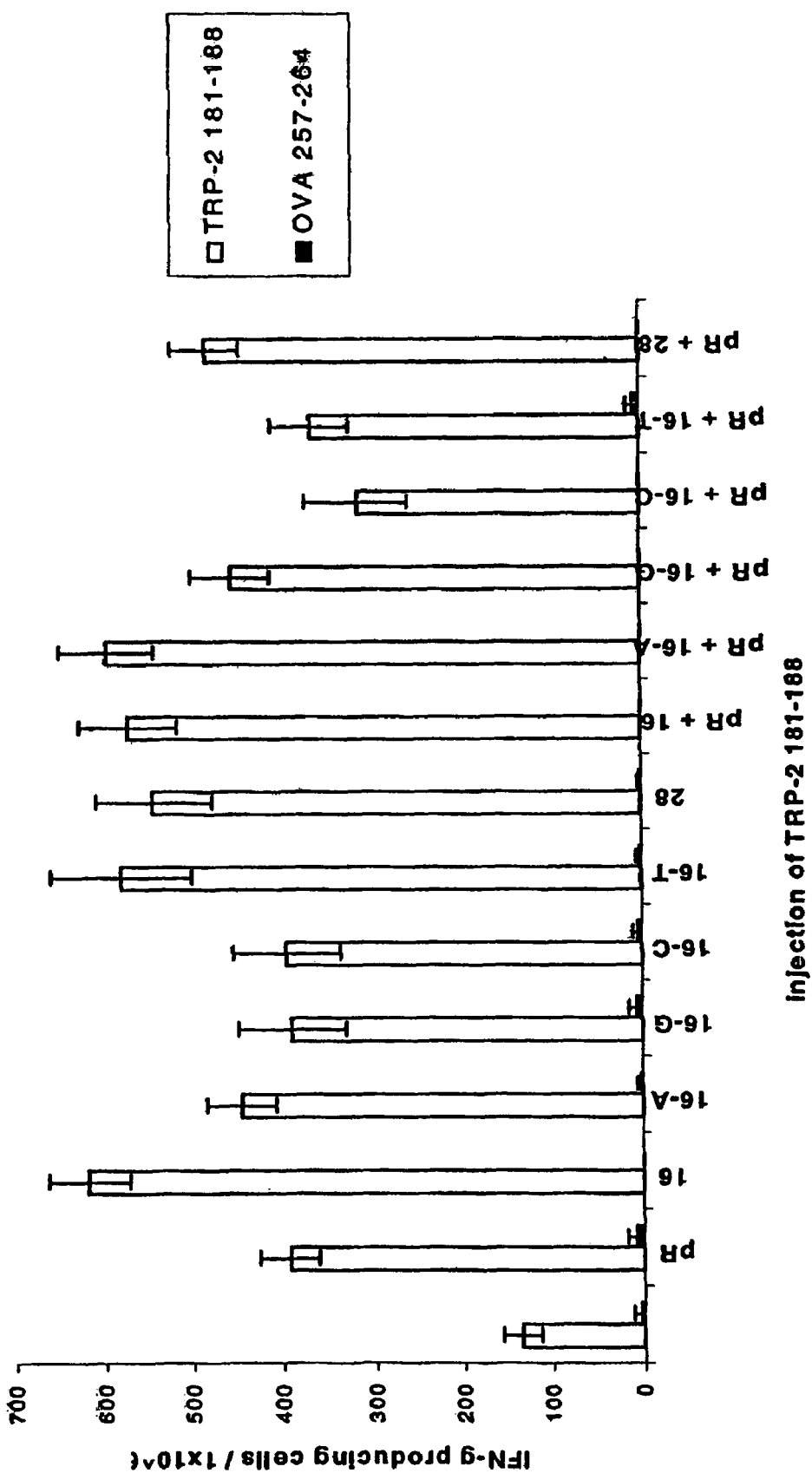
FIG. 9 shows the generation of specific immune responses against the melanoma-derived TRP-2$_{181-188}$ with different U-ODNs.

FIG. 9 clearly shows that all sequences are effective which leads to the conclusion that deoxy-Uridine containing oligonucleotides do not need any specific sequence surrounding or defined bases (e.g. a specific sequence motif) for effectiveness. This conclusion was also proven by U-ODN 21 (containing only deoxy-Uridine and deoxy-adenosine). U-ODN 22 and U-ODN 24 (which do not contain any naturally occurring DNA-bases any more). It is therefore clear, that the effectiveness of the oligonucleotides according to the present invention is based on the deoxy-Uridine itself but does not need any specific base-motifs or specific bases which occur in natural DNA.

REFERENCES

Andreu, D., and Rivas, L. (1998). Animal antimicrobial peptides: an overview. Biopolymers 47, 415-433.

Ballas, Z. K., Rasmussen, W. L., and Krieg, A. M. (1996). Induction of NK activity in murine and human cells by CpG motif in oligodeoxynucleotides and bacterial DNA. J Immunol 157, 1840-1845.

Bloom, B. R., and Widdus, R. (1998). Vaccine visions and their global impact. Nat Med 4, 480-484.

Bloom, M. B., Perry-Lalley, D., Robbins, P. F., Li, Y., el-Gamil, M., Rosenberg, S. A., and Yang, J. C. (1997). Identification of tyrosinase-related protein 2 as a tumor rejection antigen for the B 16 melanoma. J Exp Med 185, 453-459.

Buschle, M., Schmidt, W., Berger, M., Schaffner, G., Kurzbauer, R., Killisch, 1., Tiedemarm, J. K., Trska, B., Kirlappos, H., Mechtler, K., Schilcher, F., Gabler, C., and Birntsiel, M. L. (1998). Chemically defined, cell-free cancer vaccines: use of tumor antigen-derived peptides or polyepitope proteins for vaccination. Gene Ther. Mol. Biol. 1, 309-321

Buschle, M., Schmidt, W., Zauner, W., Mechtler, K., Trska, B., Kirlappos, H., and Birnstiel, M. L. (1997). Transloading of tumor antigen-derived peptides into antigen-presenting cells. Proc. Natl. Acad. Sci. USA 94, 3256-3261

Cavanaugh, P. F., Jr., Ho, Y-K, and Bardos, T. J. (1996). The activation of murine macrophages and natural killer cells by the Partially thiolated double stranded RNA poly (1). mercapto poly(C). Res. Comm. Mol. Pathol. Pharmacol. 91, 131-147

Chace, J. H., Hooker, N. A., Mildenstein, K. L., Krieg, A. M., and Cowdery, J. S. (1997). Bacterial DNA-induced NK cell IFN-gamma production is dependent on macrophage secretion of IL-12. Clin Immunol Immunopathol 84, 185-193.

Davis, H. L., Weeranta, R., Waldschmidt, T. J., Tygrett, L., Schorr, J., and Krieg, A. M. (1998). CpG DNA is a potent enhancer of specific immunity in mice immunized with recombinant hepatitis B surface antigen. J Immunol 160, 870-876.

Deng, G. M., Nilsson, I. M., Verdrengh, M., Collins, L. V., and Tarkowski, A. (1999). Intra-articularly localized bacterial DNA containing CpG motifs induces arthritis. Nat Med 5, 702-705.

Ganz, T. (1999). Defensins and host defense [comment]. Science 286, 420-421.

Ganz, T., and Lehrer, R. 1. (1999). Antibiotic peptides from higher eukaryotes: biology and applications. Mol Med Today 5, 292-297.

Hancock, R. E. (1999). Host defence (cationic) peptides: what is their future clinical potential? Drugs 57, 469-473.

Harlow, E., and Lane, D. (1988). Antibodies: a laboratory manual (Cold Spring Harbor: Cold Spring Harbor Laboratory).

Hartmann, G., Weiner, G. J., and Krieg, A. M. (1999). CpG DNA: A potent signal for growth, activation, and maturation of human dendritic cells. Proc Natl Acad Sci USA 96, 9305-9310.

Hoffmann, J. A., Kafatos, F. C., Janeway, C. A., and Ezekowitz, R. A. (1999). Phylogenetic perspectives in innate immunity. Science 284, 1313-1318.

Klinman, D. M., Yi, A. K., Beaucage, S. L., Conover, J., and Krieg, A. M. (1996). CpG motifs present in bacteria DNA rapidly induce lymphocytes to secrete interleukin 6, interleukin 12, and interferon gamma. Proc Natl Acad Sci USA 93, 2879-2883.

Krieg, A. M. (1999). CpG DNA: a novel immunomodulator [letter]. Trends Microbiol 7, 64-5.

Krieg, A. M. (1996). An innate immune defense mechanism based on the recognition of CpG motifs in microbial DNA. J Lab Clin Med 128, 128-133.

Krieg, A. M., Yi, A. K., Matson, S., Waldschmidt, T. J., Bishop, G. A., Teasdale, R., Koretzky, G. A., and Klinman, D. M. (1995). CpG motifs in bacterial DNA trigger direct B-cell activation. Nature 374, 546-549.

Krieg, A. M., Yi, A. K., Schorr, J., and Davis, H. L. (1998). The role of CpG dinucleotides in DNA vaccines. Trends Microbiol 6, 23-27.

Lethe, B., van den Eynde, B., van Pel, A., Corradin, G., and Boon, T. (1992). Mouse tumor rejection antigens P815A and P815B: two epitopes carried by a single peptide. Eur J Immunol 22, 2283-2288.

Liljeqvist, S., and Stahl, S. (1999). Production of recombinant subunit vaccines: protein immunogens, live delivery systems and nucleic acid vaccines. J Biotechnol 73, 1-33.

Lipford, G. B., Heeg, K., and Wagner, H. (1998). Bacterial DNA as immune cell activator. Trends Microbiol 6, 496-500.

Manetti, R., Annunziato, F., Tomasevic, L., Gianno, V., Parronchi, P., Romagnani, S, and Maggi, E. (1995). Polyinosinic acid: polycytidylic acid promotes T helper type 1-specific immune responses by stimulating macrophage production of interferon-α and interleukin-12. Eur. J. Immunol. 25, 2656-2660

Mosmann, T. R., Cherwinski, H., Bond, M. W., Giedlin, M. A., and Coffman, R. L. (1986). Two types of murine helper T cell clone. 1. Definition according to profiles of lymphokine activities and secreted proteins. J Immunol 136, 2348-2357.

Nossal, G. (1998). Living up to the legacy. Nat Med 4, 475-476

Oxenius, A., Martinic, M M., Hengartner, H., and Klenerman, P. (1999). CpG-containing oligonucleotides are efficient adjuvants for induction of protective antiviral immune responses with Tcell peptide vaccines. J Virol 73, 4120-4126.

Paillard, F. (1999). CpG: the double-edged sword [comment]. Hum Gene Ther 10, 2089-2090.

Pamer, E. G., Harty, J. T., and Bevan, M. J. (1991). Precise prediction of a dominant class I MHC-restricted epitope of *Listeria monocytogenes*. Nature 353, 852-855.

Parronchi, P., Brugnolo, F., Annunziato, F., Manuelli, C., Sampognaro, S., Mavilia, C., Romagnani, S., and Maggi, E. (1999). Phosphorothioate oligodeoxynucleotides promote the in vitro development of human allergen-specific CD4+ T cells into Th1 effectors. J Immunol 163. 5946-5953.

Pisetsky, D. S. (1997). Immunostimulatory DNA: a clear and present danger? Nat Med 3, 829-831.

Pisetsky, D. S. (1999). The influence of base sequence on the immunostimulatory properties of DNA. Immunol Res 19, 35-46.

Rammensee, H. G., Friede, T., Stevanoviic S. (1995), MHC ligands and peptide motifs: first listing. Immunogenetics 41, 178-228

Rodrigues, M., Nussenzweig, R. S., Romero, P., and Zavala, F. (1992). The in vivo cytotoxic activity of CD8+ T cell clones correlates with their levels of expression of adhesion molecules. J Exp Med 175, 895-905.

Roitt, 1., Brostoff, J., and Male, D. (1998). Immunology (London: Mosby International Ltd).

Rotzschke, O., Falk, K., Stevanovic, S., Jung, G., Walden, P., and Rammensee, H. G. (1991). Exact prediction of a natural T cell epitope. Eur J Immunol 21, 2891-2894.

Schmidt, W., Buschle, M., Zauner, W., Kirlappos, H., Mechtler, K., Trska, B., and Bimstiel, M. L. (1997). Cell-free tumor antigen peptide-based cancer vaccines. Proc. Natl. Acad. Sci. USA 94, 3262-3267

Schwartz, D. A., Quinn, T. J., Thorne, P. S., Sayeed, S., Yi, A. K., and Krieg, A. M. (1997). CpG motifs in bacterial DNA cause inflammation in the lower respiratory tract, J Clin Invest 100, 68-73.

Shimonkevitz, R., Colon, S., Kappler, J. W., Marrack, P., and Grey, H. M. (1984). Antigen recognition by H2-resctricted T cells 11. A tryptic ovalbumin peptide that substitutes for processed antigen. J Immunol 133, 2067-2074.

Simmaco, M., Mignogna, G., and Barra, D. (1998). Antimicrobial peptides from amphibian skin: what do they tell us? Biopolymers 47, 435-450.

Sparbier, K., and Walden, P. (1999). T cell receptor specificity and mimotopes. Curr Opin Immunol 11, 214-218.

Sparwasser, T., Koch, E. S., Vabulas, R. M., Heeg, K., Lipford, G. B., Ellwart, J. W., and Wagner, H. (1998). Bacterial DNA and immunostimulatory CpG oligonucleotides trigger maturation and activation of murine dendritic cells. Eur J Immunol 28, 2045-2054.

Sparwasser, T., Miethke, T., Lipford, G., Borschert, K., Hacker, H., Heeg, K., and Wagner, H. (1997). Bacterial DNA causes septic shock [letter]. Nature 386, 336-337.

Sparwasser, T., Miethke, T., Lipford, G., Erdmann, A., Hacker, H., Heeg, K., and Wagner, H. (1997). Macrophages sense pathogens via DNA mot)&: induction, of tumor necrosis factor-alpha-mediated shock. EurJ Immunol 27, 1671-1679.

Weiner, G. J., Liu, H. M., Wooldridge, J. E., Dahle, C. E., and Krieg, A. M. (1997). Immunostimulatory oligodeoxynucleotides containing the CpG motif are effective as immune adjuvants in tumor antigen immunization. Proc Natl Acad Sci USA 94, 10833-10837.

Yew, N. S., Wang, K. X., Przybylska, M., Bagley, R. G., Stedman, M., Marshall, J., Scheule, R. K., and Cheng, S. H. (1999). Contribution of plasmid DNA to inflammation in the lung after administration of cationic lipid:pDNA complexes. Hum Gene Ther 10, 223-234.

The invention claimed is:

1. A method of stimulating a T cell response comprising: obtaining a pharmaceutical composition comprising an antigen and an oligodeoxynucleic acid molecule (ODN) having a structure of formula (I):

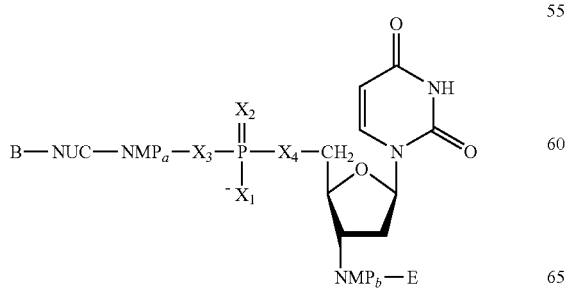

wherein:

any X is O or S;

any NMP is a 2' deoxynucleoside-monophosphate or -monothiophosphate, further defined as deoxyadenosine-, deoxyguanosine-, deoxyinosine-, deoxycytosine-, or deoxyuridine-aa deoxythymidine-, 2-methyl-deoxyinosine-, 5-methyl-deoxycytosine-, deoxypseudouridine-, 6-S-deoxyguanine-, 2-dimethyl-deoxyguanosine-, or N-isopentenyl-deoxyadenosine-monophosphate or -monothiophosphate, and wherein at least one of the NMPs immediately 5' or 3' adjacent to the deoxyuridine is a 2'-deoxycytosine-monophosphate or monothiophosphate;

NUC is a 2' deoxynucleoside, further defined as deoxyadenosine-, deoxyguanosine-, deoxyinosine-, deoxycytosine-, deoxythymidine-, 2-methyl-deoxyuridine-, 5-methyl-deoxycytosine-, deoxypseudouridine-, 6-S-deoxyguanine-, dimethyl-deoxyguanosine-, or N-isopentenyl-deoxyadenosine;

a and b are integers from 0 to 100, with the proviso that a+b is between 4 and 150; and B and E are common groups for 5' or 3' ends of nucleic acid molecules; and administering the pharmaceutical composition to a subject;

wherein the ODN does not contain a CpG motif.

2. A pharmaceutical composition comprising, in a pharmaceutically acceptable carrier, an antigen and an oligodeoxynucleic acid molecule (ODN) having a structure of formula (I):

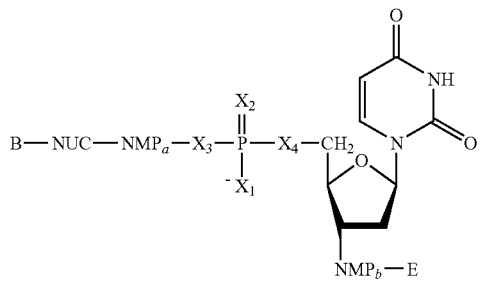

wherein:
any X is O or S;
any NMP is a 2' deoxynucleoside-monophosphate or -monothiophosphate, further defined as deoxyadenosine-, deoxyguanosine-, deoxyinosine-, deoxycytosine-, or deoxyuridine-, deoxythymidine-, 2-methyl-deoxyinosine-, 5-methyl-deoxycytosine-, deoxypseudouridine-, 6-S-deoxyguanine-, 2-dimethyl-deoxyguanosine-, or N-isopentenyl-deoxyadenosine-monophosphate or -monothiophosphate, and wherein at least one of the NMPs immediately 5' or 3' adjacent to the deoxyuridine is a 2'-deoxycytosine-monophosphate or monothiophosphate;

NUC is a 2' deoxynucleoside, further defined as deoxyadenosine-, deoxyguanosine-, deoxyinosine-, deoxycytosine-, deoxythymidine-, 2-methyl-deoxyuridine-, 5-methyl-deoxycytosine-, deoxypseudouridine-, 6-S-deoxyguanine-, 2-dimethyl-deoxyguanosine-, or N-isopentenyl-deoxyadenosine;

a and b are integers from 0 to 100, with the proviso that a+b is between 4 and 150; and B and E are common groups for 5' or 3' ends of nucleic acid molecules;

wherein the ODN does not contain a CpG motif.

3. The method of claim 1, wherein any NMP is deoxyadenosine-, deoxyguanosine-, deoxyinosine-, deoxycytosine-, deoxyuridine-, deoxythymidine-, 2-methyl-deoxyuridine-, or 5-methyl-deoxycytosine-monophosphate or -monothiophosphate.

4. The method of claim 1, wherein a+b is between 10 and 60.

5. The method of claim 4, wherein a+b is between 15 and 40.

6. The method of claim 1, wherein at least one of $X_1$ and $X_2$ is S and at least one of $X_3$ and $X_4$ is O.

7. The method of claim 6, wherein any NMP is a nucleoside-monothiophosphate.

8. The method of claim 1, wherein said ODN comprises at least one 2'deoxycytosine-monophosphate or -monothiophosphate 3'-adjacent to a 2' deoxyuridine-monophosphate or -monothiophosphate.

9. The method of claim 1, wherein said ODN comprises the sequence wdu, wherein:
u is deoxyuridine-monophosphate or -monothiophosphate;
any w is a 2' deoxynucleoside-monophosphate or -monothiophosphate, further defined as deoxyadenosine- or deoxythymidine-monophosphate or -monothiophosphate; and
any d is a T deoxynucleoside monophosphate or monothiophosphate, further defined as deoxyadenosine-, deoxyguanosine- or deoxythymidine-monophosphate or -monothiophosphate.

10. The method of claim 1, wherein B and E are independently: —H, —$CH_3$, —COH, —$COCH_3$, —OH, —CHO, —$PO_4$, —$PSO_3$, —$PS_2O_2$, —$PS_3O$, —$PS_4$, —$SO_3$, —$PO_4(CH_2)_{1-6}$—$NH_2$, or —$PO_4$—$(CH_2)_{1-6}$—NH-Label.

11. The method of claim 1, wherein the pharmaceutical composition further comprises a polycationic polymer, a synthetic peptide containing 2 KLK motifs separated by a linker of 3 to 7 hydrophobic amino acids, a growth hormone, a cytokine, an anti-inflammatory substance, an antimicrobial substance, a buffer substance, or a stabilizer.

12. The method of claim 1, wherein the pharmaceutical composition is further defined as comprising a dose of 1 ng to 1 g of the ODN.

13. The method of claim 12, wherein the pharmaceutical composition is further defined as comprising a dose of 100 ng to 10 mg of the ODN.

14. The method of claim 13, wherein the pharmaceutical composition is further defined as comprising a dose of 10 μg to 1 mg of the ODN.

15. The pharmaceutical composition of claim 2, wherein any NMP is deoxyadenosine-, deoxyguanosine-, deoxyinosine-, deoxycytosine-, deoxyuridine-, deoxythymidine-, 2-methyl-deoxyuridine-, or 5-methyl-deoxycytosine-monophosphate or monothiophosphate.

16. The pharmaceutical composition of claim 2, wherein a+b is between 10 and 60.

17. The pharmaceutical composition of claim 16, wherein a+b is between 15 and 40.

18. The pharmaceutical composition of claim 2, wherein at least one of $X_1$ and $X_2$ is S and at least one of $X_3$ and $X_4$ is O.

19. The pharmaceutical composition of claim 2, wherein any NMP is a nucleoside-monothiophosphate.

20. The pharmaceutical composition of claim 2, wherein said ODN comprises at least one 2' deoxycytosine-monophosphate or -monothiophosphate 3'-adjacent to a 2'-deoxyuridine-monophosphate or -monothiophosphate.

21. The pharmaceutical composition of claim 2, wherein said ODN comprises the sequence wdu, wherein:
u is deoxyuridine-monophosphate or -monothiophosphate;
any w is a 2' deoxynucleoside monophosphate or monothiophosphate, further defined as deoxyadenosine- or deoxythymidine-monophosphate or -monothiophosphate; and
any d is a 2' deoxynucleoside monophosphate or monothiophosphate, further defined as deoxyadenosine-, deoxyguanosine- or deoxythymidine-monophosphate or -monothiophosphate.

22. The pharmaceutical composition of claim 2, wherein B and E are independently: —H, —$CH_3$, —COH, —$COCH_3$, —OH, —CHO, —$PO_4$, —$PSO_3$, —$PS_2O_2$, —$PS_3O$, —$PS_4$, —$SO_3$, —$PO_4(CH_2)_{1-6}$, —$NH_2$, or —$PO_4$—$(CH_2)_{1-6}$—NH-Label.

23. The pharmaceutical composition of claim 2, further comprising a polycationic polymer, a synthetic peptide containing 2 KLK motifs separated by a linker of 3 to 7 hydrophobic amino acids, a growth hormone, a cytokine, an anti-inflammatory substance, an antimicrobial substance, a buffer substance, or a stabilizer.

24. The pharmaceutical composition of claim 2, further defined as comprising a dose of 1 ng to 1 g of the ODN.

25. The pharmaceutical composition of claim 24, further defined as comprising a dose of 100 ng to 10 mg of the ODN.

26. The pharmaceutical composition of claim 25, further defined as comprising a dose of 10 µg to 1 mg of the ODN.

* * * * *

UNITED STATES PATENT AND TRADEMARK OFFICE
CERTIFICATE OF CORRECTION

| | | |
|---|---|---|
| PATENT NO. | : 7,858,588 B2 | Page 1 of 1 |
| APPLICATION NO. | : 10/478771 | |
| DATED | : December 28, 2010 | |
| INVENTOR(S) | : Karen Lingnau et al. | |

It is certified that error appears in the above-identified patent and that said Letters Patent is hereby corrected as shown below:

In claim 1, column 32, line 54, delete "deoxyuridine-aa" and insert -- deoxyuridine-, -- therefor.

In claim 1, column 32, line 66, delete "dimethyl-" and insert -- 2-dimethyl -- therefor.

In claim 9, column 34, line 9, delete "T" and insert -- 2' -- therefor.

Signed and Sealed this
Eighth Day of March, 2011

David J. Kappos
*Director of the United States Patent and Trademark Office*

SEQUENCE LISTING

```
<160> NUMBER OF SEQ ID NOS: 20

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer
<220> FEATURE:
<221> NAME/KEY: modified_base
<222> LOCATION: (9)
<223> OTHER INFORMATION: N = A, C, G OR T/U

<400> SEQUENCE: 1
tccatgacnt tcctgctgat gct                                             23

<210> SEQ ID NO 2
<211> LENGTH: 20
```

```
<212> TYPE: DNA
<213> ORGANISM: Artificial Sequence
<220> FEATURE:
<221> NAME/KEY: modified_base
<222> LOCATION: (1)..(20)
<223> OTHER INFORMATION: N = A, C, G OR T/U
<220> FEATURE:
<223> OTHER INFORMATION: Description of Artificial Sequence: Synthetic
      Primer

<400> SEQUENCE: 2
nhhhhhwdnd hhhhhhhhwn                                                20

<210> SEQ ID NO 3
<211> LENGTH: 10
<212> TYPE: DNA
<213> ORGANISM: Artificial Sequence
<220> FEATURE:
<221> NAME/KEY: modified_base
<222> LOCATION: (6)
<223> OTHER INFORMATION: N = A, C, G or T/U
<220> FEATURE:
<223> OTHER INFORMATION: Description of Artificial Sequence: Synthetic
      Primer

<400> SEQUENCE: 3 hhhwdndhhh                                                           10

<210> SEQ ID NO 4
<211> LENGTH: 36
<212> TYPE: PRT
<213> ORGANISM: Mus musculus

<400> SEQUENCE: 4

Arg Leu Ala Gly Leu Leu Arg Lys Gly Gly Glu Lys Ile Gly Glu Lys
 1               5                  10                  15

Leu Lys Lys Ile Gly Gln Lys Ile Lys Asn Phe Phe Gln Lys Leu Val
            20                  25                  30

Pro Gln Pro Glu
        35

<210> SEQ ID NO 5
<211> LENGTH: 8
<212> TYPE: PRT
<213> ORGANISM: Mus musculus

<400> SEQUENCE: 5

Val Tyr Asp Phe Phe Val Trp Leu
 1               5

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 6
tccatgacgt tcctgatgct                                                20

<210> SEQ ID NO 7
<211> LENGTH: 20
<212> TYPE: DNA
<213> ORGANISM: Artificial Sequence
<220> FEATURE:
<221> NAME/KEY: modified_base
```

```
<222> LOCATION: (9)
<223> OTHER INFORMATION: N = A, C, G or T/U
<220> FEATURE:
<223> OTHER INFORMATION: Description of Artificial Sequence:  Synthetic
      Primer

<400> SEQUENCE: 7
tccatgacnt tcctgatgct                                                    20

<210> SEQ ID NO 8
<211> LENGTH: 8
<212> TYPE: PRT
<213> ORGANISM: chicken

<400> SEQUENCE: 8

Ser Ile Ile Asn Phe Glu Lys Leu
 1               5

<210> SEQ ID NO 9
<211> LENGTH: 9
<212> TYPE: PRT
<213> ORGANISM: Mus musculus

<400> SEQUENCE: 9

Leu Pro Tyr Leu Gly Trp Leu Val Phe
 1               5

<210> SEQ ID NO 10
<211> LENGTH: 26
<212> TYPE: DNA
<213> ORGANISM: Artificial Sequence
<220> FEATURE:
<221> NAME/KEY: modified_base
<222> LOCATION: (1)..(25)
<223> OTHER INFORMATION: N = A, C, G or T/U
<220> FEATURE:
<223> OTHER INFORMATION: Description of Artificial Sequence:  Synthetic
      Primer

<400> SEQUENCE: 10
nanananana nanananana nanana                                             26

<210> SEQ ID NO 11
<211> LENGTH: 26
<212> TYPE: DNA
<213> ORGANISM: Artificial Sequence
<220> FEATURE:
<221> NAME/KEY: modified_base
<222> LOCATION: (1)..(26)
<223> OTHER INFORMATION: N = A, C, G or T/U
<220> FEATURE:
<223> OTHER INFORMATION: Description of Artificial Sequence:  Synthetic
      Primer

<400> SEQUENCE: 11 nsnsnsns nsnsnsns nsnsns                                                 26

<210> SEQ ID NO 12
<211> LENGTH: 26
<212> TYPE: DNA
<213> ORGANISM: Artificial Sequence
<220> FEATURE:
<221> NAME/KEY: modified_base
<222> LOCATION: (1)..(25)
<223> OTHER INFORMATION: N = A, C, G or T/U
<220> FEATURE:
<223> OTHER INFORMATION: Description of Artificial Sequence:  Synthetic
      Primer
```

```
<400> SEQUENCE: 12
nnnnnnnnnn nnnnnnnnnn nnnnnt                                          26

<210> SEQ ID NO 13
<211> LENGTH: 10
<212> TYPE: DNA
<213> ORGANISM: Artificial Sequence
<220> FEATURE:
<221> NAME/KEY: modified_base
<222> LOCATION: (6)
<223> OTHER INFORMATION: N = A, C, G or T/U
<220> FEATURE:
<223> OTHER INFORMATION: Description of Artificial Sequence: Synthetic
      Primer

<400> SEQUENCE: 13 aaabcncaaa                                                            10

<210> SEQ ID NO 14
<211> LENGTH: 10
<212> TYPE: DNA
<213> ORGANISM: Artificial Sequence
<220> FEATURE:
<221> NAME/KEY: modified_base
<222> LOCATION: (6)
<223> OTHER INFORMATION: N = A, C, G or T/U
<220> FEATURE:
<223> OTHER INFORMATION: Description of Artificial Sequence: Synthetic
      Primer

<400> SEQUENCE: 14 hhhwwnwhhh                                                            10

<210> SEQ ID NO 15
<211> LENGTH: 10
<212> TYPE: DNA
<213> ORGANISM: Artificial Sequence
<220> FEATURE:
<223> OTHER INFORMATION: Description of Artificial Sequence: Synthetic
      Primer
<220> FEATURE:
<221> NAME/KEY: modified_base
<222> LOCATION: (6)
<223> OTHER INFORMATION: N = A, C, G or T/U

<400> SEQUENCE: 15 wwwwdndwww                                                            10

<210> SEQ ID NO 16
<211> LENGTH: 10
<212> TYPE: DNA
<213> ORGANISM: Artificial Sequence
<220> FEATURE:
<221> NAME/KEY: modified_base
<222> LOCATION: (6)
<223> OTHER INFORMATION: N = A, C, G or T/U
<220> FEATURE:
<223> OTHER INFORMATION: Description of Artificial Sequence: Synthetic
      Primer

<400> SEQUENCE: 16 sssagngsss                                                            10

<210> SEQ ID NO 17
<211> LENGTH: 10
<212> TYPE: DNA
<213> ORGANISM: Artificial Sequence
<220> FEATURE:
<221> NAME/KEY: modified_base
```

```
<222> LOCATION: (6)
<223> OTHER INFORMATION: N = A, C, G or T/U
<220> FEATURE:
<223> OTHER INFORMATION: Description of Artificial Sequence: Synthetic
      Primer

<400> SEQUENCE: 17 hhhtdndhhy                                                                 10

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 18

Ser Tyr Val Pro Ser Ala Glu Gln Ile
 1               5

<210> SEQ ID NO 19
<211> LENGTH: 10
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 19 hhhwdddhhh                                                                 10

<210> SEQ ID NO 20
<211> LENGTH: 26
<212> TYPE: RNA
<213> ORGANISM: Artificial Sequence
<220> FEATURE:
<221> NAME/KEY: modified_base
<222> LOCATION: (2,4,6,8,10,12,14,16,18,20,22,24)
<223> OTHER INFORMATION: N = inosine
<220> FEATURE:
<223> OTHER INFORMATION: Description of Artificial Sequence: Synthetic
      Primer

<400> SEQUENCE: 20 unununun unununun ununug                                                   26
```